(12) United States Patent
Beaumont

(10) Patent No.: US 10,191,029 B2
(45) Date of Patent: Jan. 29, 2019

(54) METHOD AND SYSTEM TO EXTEND THE CONDITIONS OF APPLICATION OF AN INVERSION OF THE HODGKIN-HUXLEY GATING MODEL

(71) Applicant: Jacques Beaumont, Liverpool, NY (US)

(72) Inventor: Jacques Beaumont, Liverpool, NY (US)

( * ) Notice: Subject to any disclaimer, the term of this patent is extended or adjusted under 35 U.S.C. 154(b) by 323 days.

(21) Appl. No.: 14/689,653

(22) Filed: Apr. 17, 2015

(65) Prior Publication Data

US 2015/0302169 A1 Oct. 22, 2015

Related U.S. Application Data

(60) Provisional application No. 61/981,000, filed on Apr. 17, 2014.

(51) Int. Cl.
*G01N 33/487* (2006.01)

(52) U.S. Cl.
CPC ............... *G01N 33/48728* (2013.01)

(58) Field of Classification Search
None
See application file for complete search history.

(56) References Cited

PUBLICATIONS

Csercsik, D. et al. Hodgkin-Huxley type modelling and parameter estimation of GnRH neurons. Biosystems 100, 198-207 (2010).*
Halliwell, J. V., Plant, T. D., Robbins, J. & Standen, N. B. in Microelectrode Techniques: The Plymouth Workshop Handbook 17-35 (The Company of Biologists Limited, 1994).*
Hodgkin, A. L. & Huxley, A. F. A quantitative description of membrane current and its application to conduction and excitation in nerve. The Journal of Physiology 117, 500-544 (1952).*
Hodgkin, A. L., Huxley, A. F. & Katz, B. Measurement of current-voltage relations in the membrane of the giant axon of Loligo. The Journal of Physiology 116, 424-448 (1952).*
Jackson, M. B. Whole-cell voltage clamp recording. in Current Protocols in Neuroscience 6.6.1-30 (John Wiley & Sons, Inc., 2001).*
Lee, J., Smaill, B. H. & Smith, N. Hodgkin-Huxley type ion channel characterization: An improved method of voltage clamp experiment parameter estimation. Journal of Theoretical Biology 242, 123-134 (2006).*
Mascagni, M. The Backward Euler Method for Numerical Solution of the Hodgkin-Huxley Equations of Nerve Conduction. SIAM Journal on Numerical Analysis 27, 941-962 (1990).*
Raba, A. E., Cordeiro, J. M., Antzelevitch, C. & Beaumont, J. Extending the Conditions of Application of an Inversion of the Hodgkin-Huxley Gating Model. Bulletin of Mathematical Biology 75, 752-773 (2013).*
Wang, G. J. & Beaumont, J. Parameter Estimation of the Hodgkin-Huxley Gating Model: An Inversion Procedure. SIAM Journal on Applied Mathematics 64, 1249-1267 (2004).*
Willms, A. R. NEUROFIT: Software for fitting Hodgkin-Huxley models to voltage-clamp data. Journal of Neuroscience Methods 121, 139-150 (2002).*
Belluzzi, O., Sacchi, O. & Wanke, E. A fast transient outward current in the rat sympathetic neurone studied under voltage-clamp conditions. The Journal of Physiology 358, 91-108 (1985).*
Geduldig, D. & Gruener, R. Voltage clamp of the Aplysia giant neurone: early sodium and calcium currents. The Journal of Physiology 211, 217-244 (1970).*
Hagiwara, S., Ozawa, S. & Sand, O. Voltage clamp analysis of two inward current mechanisms in the egg cell membrane of a starfish. The Journal of General Physiology 65, 617-644 (1975).*
Magura, I. S. & Kryshtal, O. A. Effect of conditioning polarization of soma of giant neurons of mollusks on the mechanism of action-potential generation. Neurophysiology 2, 72-78 (1971).*
Nelson, M. & Rinzel, J. The Hodgkin-Huxley Model. Chapter 4 of the Book of Genesis 29-49 (Springer New York, 1998).*
Standen, N. B. Voltage-clamp studies of the calcium inward current in an identified snail neurone: comparison with the sodium inward current. The Journal of Physiology 249, 253-268 (1975).*
Beaumont, J., et al. "Spiral Waves in Two-Dimensional Models of Ventricular Muscle: Formation of a Stationary Core," Jul. 1998, vol. 75 (pp. 1-14).
Beaumont, J. et al., "Estimation of the Steady-State Characteristics of the Hodgkin-Huxley Model from Voltage-Clamp Data," 1993, Mathematical Biosciences, vol. 115 (pp. 145-186).
Beaumont, J., et al., "On the Interpretation of Voltage-Clamp Data Using the Hodgkin-Huxley Model," 1993, Mathematical Biosciences, vol. 115 (pp. 65-101).
Cordeiro, J.M., et al., "Functionally distinct sodium channels in ventricular epicardial and endocardial cells contribute to a geater sensitivity of the epicardium to electrical depression," 2008, Amercian Journal of Physiology Heart and Circulatory Physiology, vol. 295 (pp. H154-H162).
Ebihara, L., et al., "Fast Sodium Current in Cardiac Muscle a Quantitative Description," 1980, Biophysical Journal, vol. 32 (pp. 779-790).

(Continued)

*Primary Examiner* — Soren Harward
(74) *Attorney, Agent, or Firm* — Harris Beach PLLC

(57) ABSTRACT

A method to quantify kinetics of voltage gated membrane channels by inversion of a Hodgkin Huxley formalism includes the steps of: providing an electrophysiology apparatus configured to provide a constant voltage difference across a cell membrane of a cell and to measure a current through the cell membrane and a computer configured to run at least one or more protocols; bounding R based on data generated by a T-step protocol or a G-step protocol; estimating a steady state based on data generated by a C-step protocol or a H step protocol; extracting a time constant based on the data generated by the T-step protocol or the G-step protocol as bounded by R; and assessing a range of time constants that can reproduce the data generated by the C-step protocol or the H step protocol and by the T-step protocol or the G-step protocol within and experimental error. C-step and a G-step voltage clamp stimulation protocols to generate a set of experimental data to quantify a channel availability of a cell are also described.

8 Claims, 20 Drawing Sheets

(56) References Cited

PUBLICATIONS

Ermentrout, G.B., et al., "The Hodgkin-Huxley Equations," 2010, Interdisciplinary Applied Mathematics, vol. 35 (pp. 1-28).

Grandi, E., et al., "A novel computational model of the human ventricular action potential and Ca transient," 2010, Journal of Molecular and Cellular Cardiology, vol. 48 (pp. 112-121).

McCormick, D., et al., "Neurophysiology: Hodgkin and Huxley model—still standing?" 2007, Nature, vol. 445 (pp. E1-E2).

Murphy, L., et al., "Extracellular proton depression of peak and late $Na^{30}$ current in the canine left ventricle," 2011, American Journal of Physiology Heart and Circulatory Physiology, vol. 301 (pp. H936-H944).

Noble, D., et al., "How the Hodgkin-Huxley equations inspired the Cardiac Physiome Project," 2012, Journal of Physiology (pp. 2613-2628).

O'Hara, T., et al., "Simulation of the Undiseased Human Cardiac Ventricular Action Potential: Model Formulation and Experimental Validation," 2011, PLoS Computational Biology, vol. 7 (pp. 1-29).

Sobie, Eric, A., "Parameter Sensitivity Analysis in Elecrophysiological Models Using Multivariable Regression," 2009, Biophysical Journal, vol. 96 (pp. 1264-1274).

Willms, A. R., et al., "An Improved Parameter Estimation Method for Hodgkin-Huxley Models," 1999, Journal of Computational Neuroscience, vol. 6 (pp. 145-168).

Hamill, O.P., et al., "Improved Patch-Clamp Techniques for High-Rsolution Current Recording from Cells and Cell-Free Membrane Patches," 1981, Pflügers Arch., vol. 391 (pp. 85-100).

Finkel, A. S., et al., "Optimal Voltage Clamping With Single Microelectrode," 1985, Voltage and Patch Clamping with Microelectrodes (pp. 95-120).

Finkel, A.S., et al., "Conventional Voltage Clamping With Two Intracellular Microelectrodes," 1985, Voltage and Patch Clamping with Microelectrodes (pp. 47-94).

Smith, Jr., T.G., et al., "Voltage and Patch Clamping With Microelectrodes," 1985, American Physiological Society (26 pgs.).

* cited by examiner

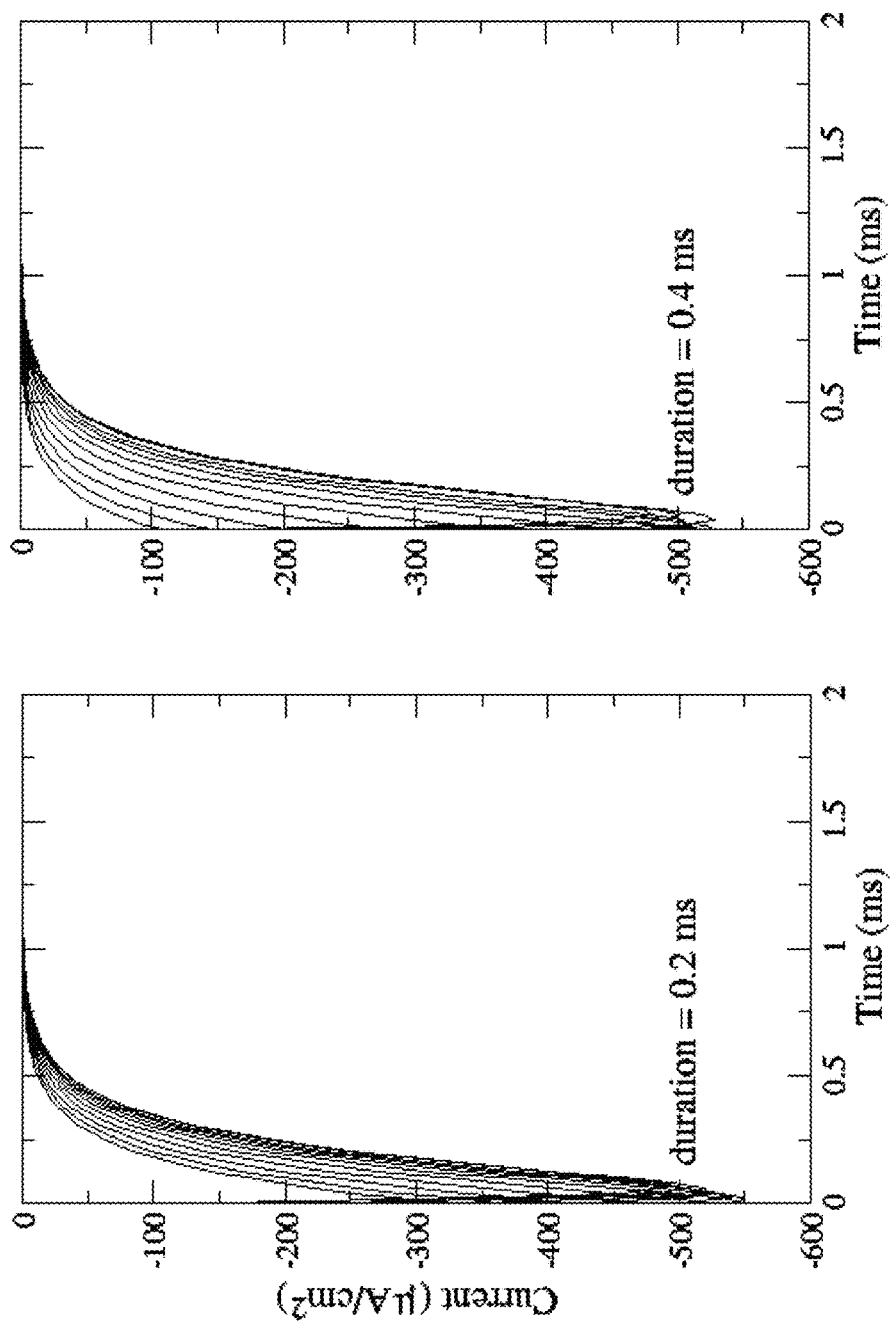

METHOD AND SYSTEM TO EXTEND THE CONDITIONS OF APPLICATION OF AN INVERSION OF THE HODGKIN-HUXLEY GATING MODEL

CROSS-REFERENCE TO RELATED APPLICATIONS

This application claims priority to and the benefit of co-pending U.S. provisional patent application Ser. No. 61/981,000, METHOD AND SYSTEM TO EXTEND THE CONDITIONS OF APPLICATION OF AN INVERSION OF THE HODGKIN-HUXLEY GATING MODEL, filed Apr. 17, 2014, which application is incorporated herein by reference in its entirety.

STATEMENT REGARDING FEDERALLY FUNDED RESEARCH OR DEVELOPMENT

This invention was made with government support under grant TG-BCS110013 awarded by the National Science Foundation and the Heart Lung and Blood Institute of the National Institutes of Health grant HL-47678. The government has certain rights in the invention.

FIELD OF THE INVENTION

The invention relates to cellular electrophysiology and more particularly to the Hodgkin-Huxley gating model.

BACKGROUND

In the background, other than the bolded paragraph numbers, non-bolded square brackets ("[ ]") refer to the citations listed hereinbelow.

Despite the limitations and empirical nature of the Hodgkin-Huxley (HH) formalism [11], it is still a foundation for numerous models in cellular electrophysiology [14]. The extensive use of the formalism can be appreciated consulting the electrophysiology section of the CellML project [16], and the web sites of groups offering a computational infrastructure for the simulation of cellular electrical activity [16, 13, 10, 5]. As a matter of fact the formalism was still employed in the most recently developed cell models [18, 9].

The foregoing and other objects, aspects, features, and advantages of the invention will become more apparent from the following description and from the claims.

SUMMARY

According to one aspect, a method to quantify kinetics of voltage gated membrane channels by inversion of a Hodgkin Huxley formalism includes the steps of: providing an electrophysiology apparatus configured to provide a constant voltage difference across a cell membrane of a cell and to measure a current through the cell membrane and a computer configured to run at least one or more protocols of a C-step protocol, an H step protocol, a T-step protocol, and a G-step protocol; bounding R based on data generated by the T-step protocol or the G-step protocol; estimating a steady state based on data generated by the C-step protocol or the H step protocol; extracting a time constant based on the data generated by the T-step protocol or the G-step protocol as bounded by R; and assessing a range of time constants that can reproduce the data generated by the C-step protocol or the H step protocol and by the T-step protocol or the G-step protocol within and experimental error.

According to another aspect, a method to quantify a channel availability of a cell includes the steps of: providing an electrophysiology apparatus configured to provide a constant voltage difference across a cell membrane of a cell and to measure a current through the cell membrane and a computer configured to run one or more processes including an inversion process of a set of underlying ordinary differential equations; applying the voltage difference across the cell membrane as a holding voltage to reach a steady state according to a protocol while recording at a time interval the voltage difference, and a measured current; changing the voltage difference across the cell membrane in a stepped manner according to the protocol while continuing to record at a time interval the voltage difference, and the measured current; repeating at least once according to the protocol with a different stepped parameter, the steps of applying the voltage difference across the cell membrane as a holding voltage to changing the voltage difference across the cell membrane to generate a data set as a solution of the set of underlying ordinary differential equations, the data set including a set of the voltage difference, and the measured current; and estimating by the inversion process a set of gating parameters including a steady state as a function of voltage and a time constant as a function of voltage and a channel conductance parameter based on the data set to quantify the channel availability of the cell.

In one embodiment, the step of repeating at least once includes repeating at least once according to the protocol with a different stepped parameter according to a H-step protocol.

In another embodiment, the step of repeating at least once includes the step of repeating at least once according to the protocol with a different stepped parameter according to a T-step protocol.

In yet another embodiment, the step of repeating at least once includes the step of repeating at least once according to the protocol with a different stepped parameter according to a C-step protocol.

In yet another embodiment, the step of repeating at least once includes the step of repeating at least once according to the protocol with a different stepped parameter according to a G-step protocol.

In yet another embodiment, the step of repeating at least once includes the step of repeating at least once according to the protocol with a different stepped voltage parameter.

In yet another embodiment, the step of repeating at least once includes the step of repeating at least once according to the protocol with a different stepped time parameter.

According to yet another aspect, a C-step voltage clamp stimulation protocol to generate a set of experimental data to quantify a channel availability of a cell includes the steps of: providing an electrophysiology apparatus configured to provide a constant voltage difference across a cell membrane of a cell and to measure a current through the cell membrane and a computer configured to run one or more processes including a voltage stepping process and a process configured to control a stepped parameter including a voltage parameter or a time parameter; applying the voltage difference across the cell membrane as a holding voltage to reach a steady state according to the protocol while recording at a time interval the voltage difference, and a measured current; changing by the computer the voltage difference across the cell membrane in a stepped manner according to the protocol to a conditioning potential while continuing to record at a time interval the voltage difference and the measured current; changing by the computer the voltage difference across the cell membrane in a stepped manner according to the protocol to a test potential while continuing to record at a time interval the voltage difference and the measured current; and repeating at least once according to the protocol with a different stepped parameter, the steps of applying the voltage difference across the cell membrane as a holding voltage to changing by the computer the voltage difference across the cell membrane in a stepped manner according to the protocol to a test potential to generate a data set as a solution of the set of underlying ordinary differential equations, the data set including a set of the voltage difference and the measured current.

According to yet another aspect, a G-step voltage clamp stimulation protocol to generate a set of experimental data to quantify a channel availability of a cell include the steps of: providing an electrophysiology apparatus configured to provide a constant voltage difference across a cell membrane of a cell and to measure a current through the cell membrane and a computer configured to run one or more processes including a voltage stepping process and a process configured to control a stepped parameter including a voltage parameter or a time parameter; applying the voltage difference across the cell membrane as a holding voltage to reach a steady state according to the protocol while recording at a time interval the voltage difference and a measured current; changing by the computer the voltage difference across the cell membrane in a stepped manner according to the protocol to a conditioning potential while continuing to record at a time interval the voltage difference and the measured current; changing by the computer the voltage difference across the cell membrane in a stepped manner according to the protocol to a gap potential while continuing to record at a time interval the voltage difference and the measured current; changing by the computer the voltage difference across the cell membrane in a stepped manner according to the protocol to a test potential while continuing to record at a time interval the voltage difference and the measured current; and repeating at least once according to the protocol with a different gap stepped parameter, the steps of applying the voltage difference across the cell membrane as a holding voltage to changing by the computer the voltage difference across the cell membrane in a stepped manner according to the protocol to a test potential to generate a data set as a solution of the set of underlying ordinary differential equations, the data set including a set of the voltage difference and the measured current.

According to yet another aspect, a system to quantify a channel availability of a cell includes an electrophysiology apparatus configured to provide a constant voltage difference across a cell membrane of a cell and to measure a current through the cell membrane; a computer configured to run one or more processes including an inversion process of a set of underlying ordinary differential equations; and wherein the computer is configured to cause the electrophysiology apparatus to apply the voltage difference across the cell membrane as a holding voltage to reach a steady state according to a protocol while recording at a time interval the voltage difference, a measured current, and a time, to change the voltage difference across the cell membrane in a stepped manner according to the protocol while continuing to record at a time interval the voltage difference and the measured current, to repeat the protocol at least once with a different stepped parameter to generate a data set as a solution of the set of underlying ordinary differential equations, the data set including a set of the voltage difference and the measured current, and to estimate by the inversion process a set of gating parameters including a steady state as a function of voltage and a time constant as a function of voltage and a channel conductance parameter based on the data set to quantify the channel availability of the cell.

According to yet another aspect, a method to quantify channel kinetics includes the steps of: providing an electrophysiology apparatus configured to provide a constant voltage difference across a cell membrane of a cell and to measure a current through the cell membrane and a computer configured to run one or more processes including an inversion process of a set of underlying ordinary differential equations; applying the voltage difference across the cell membrane according to a protocol while recording at a time interval the voltage difference, and a measured current to generate a data set as a solution of the set of underlying ordinary differential equations, the data set including a set of the voltage difference, and the measured current; and estimating by the inversion process a set of gating parameters including a steady state as a function of voltage and a time constant as a function of voltage and a channel conductance parameter based on the data set to quantify channel kinetics The foregoing and other aspects, features, and advantages of the application will become more apparent from the following description and from the claims.

BRIEF DESCRIPTION OF THE DRAWINGS

The features of the application can be better understood with reference to the drawings described below, and the claims. The drawings are not necessarily to scale, emphasis instead generally being placed upon illustrating the principles described herein. In the drawings, like numerals are used to indicate like parts throughout the various views.

FIG. 11A show a graph of current vs. time generated by the Ebihara and Johnson sodium model subjected to the C-step stimulation protocol with conditioning pulse duration of 0.2 ms;

FIG. 11B show a graph of current vs. time generated by the Ebihara and Johnson sodium model subjected to the C-step stimulation protocol with conditioning pulse duration of 0.4 ms;

DETAILED DESCRIPTION

Figure 1A:
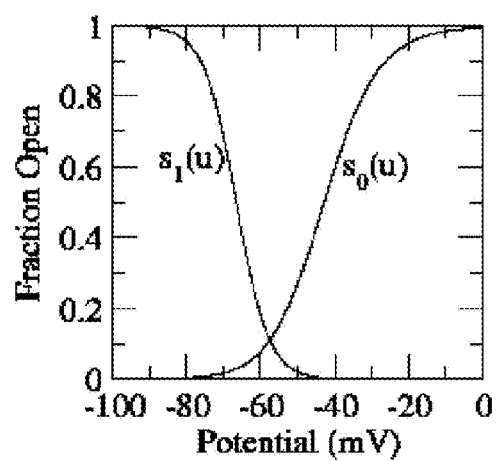
FIG. 1A shows an exemplary graph of the voltage dependence of the steady state of the gating variables vs. potential for the Ebihara and Johnson current model of the cardiac sodium current.

In the text of the detailed description, not including mathematical expressions, other than the bolded paragraph numbers, non-bolded square brackets ("[ ]") refer to the citations listed hereinbelow.

A new method and system for the estimation of the parameters and functions of voltage, which are denoted by "gating parameters", of the Hodgkin Huxley formalism is described hereinbelow. The formalism is a nonlinear ordinary differential equation (ODE) with few state variables, so far not more than 3, which is used to quantify the kinetics of voltage gated membrane channels. Membrane channels are proteins embedded in cell membranes which control the passage of specific ion species in and out of a cell or any other compartment delimited by a membrane. A large number of membrane channels are voltage gated. This means that under the influence of membrane voltage some protein domains move in the electrostatic field, change the channel configuration, and the conductance of this one. In other words, the pore region of the membrane channel opens and closes with changes in membrane potential, causing changes in conductance. The rate at which channels open and close is a main determinant of the dynamical properties of a cell, or an entity delimited by a membrane, and can be quantified by the Hodgkin-Huxley formalism.

The new system and method described hereinbelow can be applied to a given type of channel, i.e., channels that activate and inactivate with changes of membrane voltage, such as, for example, the sodium channel of excitable cell membranes. Such voltage gated channels can be described with Hodgkin-Huxley formalism of two state variables. The underlying differential equation includes two functions of voltage for each state variable, i.e., the voltage dependence of the steady state, and time constant. And, a parameter, the channel conductance. All together the four functions of voltage (steady state and time constant for each state variable), and the conductance, termed the "gating parameters" are unknown, and should be estimated from experimental data. They cannot be estimated from first principle.

Definitions:

steady state as used herein generally refers to a distribution of open and closed channels at a given a voltage after the voltage has been maintained long enough beyond several time constants.

time constant is the rate at which the channels open and close.

resistance is the inverse of conductance. The terms resistance and conductance are used interchangeably throughout.

The estimation of the gating parameters of the Hodgkin Huxley formalism can be estimated by use of nonlinear least square fitting. Specifically, in a computer model, the Hodgkin-Huxley formalism is subjected to the same electrical stimulation as in the experiment. The model prediction for a given set of gating parameters and experimental data, i.e., a set of current traces in time, is compared. The basis of the comparison is least square, meaning that for each sample point (time and voltage changed) the difference between the experiment and model data are squared and summed. The number generated this way is a measure of the similarity between the experimental and model data. By repeating this comparison for different gating parameters one generates a multidimensional function, the dimension of which is equal to the number of gating parameters to estimate, is called the objective function. The dimension of the objective function is relatively large because the unknown functions of voltage are parameterized. The image of the objective function is the least square value that measures similarity between experimental and model data.

In this context, the estimation problem is to find in the parameter space (domain of the multidimensional objective function) the coordinate for which the least square value is minimal, i.e., one has to find the minimum of the objective function. The problem is nonlinear because the objective function is a nonlinear expression of the unknown gating parameters. Consequently the search for the minimum cannot be reduced to the solution of a matrix system. Instead it should be done iteratively. The objective function is evaluated at a point in the parameter space and the search algorithm moves a small step in the direction of the objective function gradient towards the minimum. The function value and its gradient at each point are used to estimate the best displacement direction.

There are several limitations with this approach. They are essentially due to the fact that the objective function is multidimensional and nonlinear. I described these limitations in previous articles. [3, 4, 20]. However it is possible. Basically a quality estimation should address the following three questions: (i) does the data generated constrain the estimation problem, i.e., is the data set complete, (ii) if it does, can an optimal set of parameters be found in a reliable manner (minimum of objective function), and (iii) how does the method cope with the potential ill posed nature of the problem (a small experimental error can generate a large variation on the gating parameters)? Nonlinear least square fitting cannot address any of these questions because there is no way to know whether the data generated sufficiently constrain the parameters. Even if it does due to the multidimensionality of the objective function, it is not known whether the minimum found is the global minimum. Finally there are no elegant ways to cope with the ill posed nature of the problem. Once a set of gating parameters is found, the gating parameters can be perturbed. It is then possible to observe changes in the least square error. However, the ill posed nature may exist only in a specific direction, along a curve, or in a nonlinear manifold of the parameter space. Yet, this subspace cannot be determined when the dimension of the objective function is large, which is the case here.

I previously introduced an estimation method that alleviates all limitations inherent to nonlinear least square [3, 4, 20]. It is based on an inversion of the underlying differential equations. The estimation method replaces the search for the minimum of multidimensional objective function by a set of transformations applied on the experimental data. These transformations are based on an inversion of the underlying differential equation. It takes the experimental data as the solution of the differential equation, and applies a sequence of transformations that recovers the gating parameters including initial conditions. The method allows one to answer conclusively the three basic questions (i) to (iii) raised hereinabove.

While the inversion method is powerful, as initially published [3, 4, 20] it has limited application. In the previous publications, data at the basis of the estimation were generated by stimulating cells with one or multiple step voltage stimulations. However, due to experimental constraints some of the protocols are not applicable. For example, one of the previous protocols required the membrane voltage to be maintained at large depolarization potential for an interval of time sufficiently long to reach steady state. For most cells it is not possible to meet this condition because at high potential cells are leaky and the large influx of ions in such conditions kills the cell.

Among other aspects, cells cannot be maintained at large depolarized potential for long intervals of time. Therefore, what is needed is a new method and system less damaging to cells and compatible with protocols that can generate complete data sets.

The solution described in more detail hereinbelow includes a new series of step voltage clamp stimulations that are practical and can be used to generate complete data sets for channel exhibiting activation and inactivation. Also, the inversion procedure has been extended to process the data produced by these protocols in a manner to recover the gating parameters from an inversion of the Hodgkin-Huxley formalism. In addition, so far gating parameter estimation has been problematic for channels inactivating rapidly at potentials closed to the rest potential. The new system and method described herein addresses this problem, and is applicable to channels of excitable tissue known so far. Exemplary protocols of the new system and method are described in more detail herein below, in particular with respect to stimulation protocols illustrated by FIG. 10A, FIG. 10C, FIG. 12A and FIG. 12C. Specifically, the new Lemma describes how the inversion method was extended to process the newly generated data by use of the new system and method described herein.

As discussed hereinabove in the background section, despite the limitations and empirical nature of the Hodgkin-Huxley (HH) formalism [11], it is still a foundation for numerous models in cellular electrophysiology [14]. The extensive use of the formalism can be appreciated consulting the electrophysiology section of the CellML project [16], and the web sites of groups offering a computational infrastructure for the simulation of cellular electrical activity [16, 13, 10, 5]. The formalism was still employed in the most recently developed cell models [18, 9].

Furthermore, there are increasing efforts to incorporate such cell models in large scale models of tissues and organs [1] which may constitute one of the most valuable tools to capitalize on the genome on our quest to decipher the molecular mechanisms of a number of diseases [17]. In this context, the estimation of the parameters, including functions of voltage, of the HH formalism is a cornerstone, as it limits the reliability of the macroscopic level simulations. This point is well illustrated by the fact that relatively small perturbations in the HH formalism parameter values, if done in the appropriate direction in the parameter space, can make a dramatic change on wave dynamics [2]. It remains to know whether perturbations in parameter values producing significant changes in wave dynamics are within experimental error.

The reader unfamiliar with the Hodgkin Huxley formalism may consult Ermentrout [8, section 1.8] for a detailed description. Currents analyzed in this manuscript display activation and inactivation and are hence modeled with two state variables. For this case, the unknowns are one parameter (the maximal channel conductance) and two functions of voltage, the steady state and time constant, for each state variable (a total of 4 functions). Two of these four functions specify the initial values. Because the unknowns include functions of voltage and a parameter, to avoid confusion, we refer to the unknowns as the gating model parameters (GMP).

The new method to estimate the gating parameters described herein is based on an inversion of the Hodgkin-Huxley formalism. This work was initiated in [4,3] where inversion was based on peak currents exclusively. It was extended later [20] to consider the entire interval of acquisition but with some limitations. Some of the stimulations protocol are not applicable without damaging the cell. In addition the method was not applicable to channels that rapidly inactivate in a given potential range. This is the case for the sodium channel of most excitable tissues which inactivate rapidly at potentials near the rest potential. The new method described herein overcomes these limitations.

In Part 2 the inversion is described and its limitation discussed, in Part 3 the acquisition and pre-processing of Biological data is described, in Part 4, the inversion is applied to incomplete Biological data and complete synthetic data, as well as explain how the limitations of the current version of the inversion are overcome. Part 5 is a summary and conclusion.

Part 2 Inversion of the HH Formalism and its Limitations

The Hodgkin-Huxley formalism for an activating and inactivating ionic current is given by, $$I(u, t) = \bar{g} y_0^{\lambda_0} y_1^{\lambda_1} (u - e) \quad (1)$$

$$\frac{dy_i(u, t)}{dt} = \frac{s_i(u) - y_i(u, t)}{\tau_i(u)} i \in [0, 1] \quad (2)$$

where u is the membrane potential, I(u, t) the ionic current, $\bar{g}$ the maximal channel conductance (open state conductance), and e the equilibrium potential. The state variables $y_i$, $i \in [0,1]$ are termed the gating variables. They represent the fraction of the population of molecular gates in the open state. The parameters $\lambda_i$, $i \in [0,1]$, are integers meant to represent the number of gating particles in the channel. These parameters are assumed to be small integers between 1 and 5, and the estimation procedure is repeated for each set of integers. Each inversion solution is associated with a range, which should be non-null and small for a set of $\lambda_i$ if the data sufficiently constrains the estimation problem. When the data does not sufficiently constrain the estimation problem, the optimal inverse solution is the one giving the greatest range. The functions of voltage $s_i(u)$ and $\tau_i(u)$ $i \in [0,1]$ are the steady states and time constants of each gating variable. In general $s_i(u)$ is sigmoidal.

Our analysis was restricted to channels having two gates. The two gates are called activation and inactivation gates because they open (ds(u)/du>0) and close (ds(u)/du<0) with depolarization. We assign the index 0 to the activation gate and 1 to the inactivation gate.

A cell membrane has a rest potential where the algebraic sum of all transmembrane currents is null. A voltage clamp stimulation is usually performed with a step voltage stimulation from a potential near the rest potential to a test potential. Specifically in a typical stimulation the membrane voltage is clamped until steady state is reached ($u_H$ : for holding potential) and then stepped to a membrane voltage termed the test potential $U_T$ from which point the current is monitored. H-step and T-step stimulation protocols are referred to where the holding and test potentials are varied respectively, while the other potential is kept constant. The range of each protocol denoted by $R_H$ and $R_T$ respectively is the potential over which $u_H$ (H-step) or $u_T$ (T-step) is varied. In such conditions, the time course of the gating variables is given by, $$y_i(t; u_H, u_T) = s_i(u_T) + (s_i(u_H) - s_i(u_T)) e^{-t/\tau_i(u_T)}, i \in [0,1]. \quad (3)$$

The estimation problem estimates the parameters $\bar{g}$, and functions $s_i(u)$, $\tau_i(U)$, $i \in [0,1]$ from experimental recordings gathered in isolated cells during voltage clamp stimulation. Note that these unknowns are referred to as the gating parameters. Because the parameters $\lambda_i$ $i \in [0,1]$ can take only few integer values, we simply repeat the estimation process for all possible combinations within the range [1,5]. The set of $\lambda_i$ providing the greatest invertible range for R are used in the subsequent steps of the estimation.

Figure 1B:
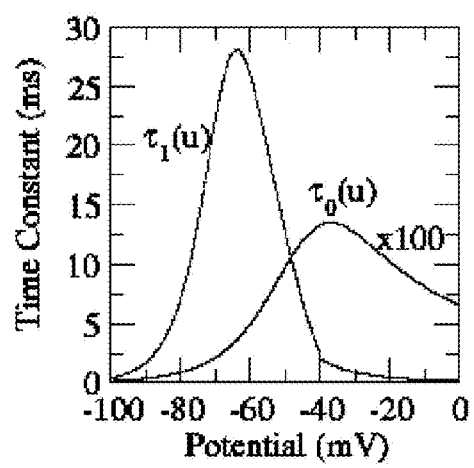
FIG. 1B shows an exemplary graph of the time constants of gating variables vs. potential for the model for the Ebihara and Johnson current model of the cardiac sodium current.
Figure 1C:
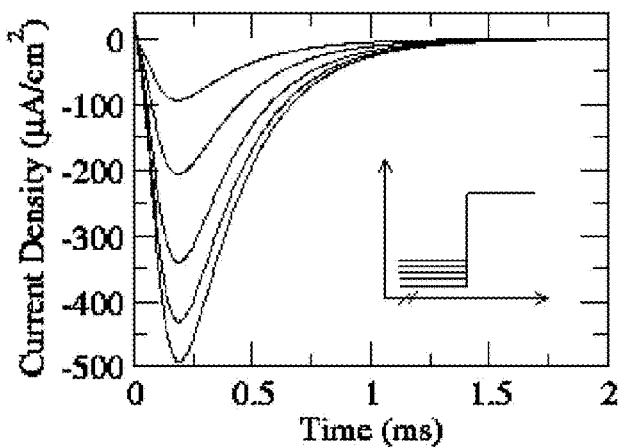
FIG. 1C shows an exemplary graph of current vs time for various test potentials generated by the Ebihara and Johnson model of the cardiac sodium current.

The procedures are tested with Biological data in Part 4.1 and with synthetic data generated by the Ebihara and Johnson model [7] of the cardiac sodium current in Part 4.2. The model is illustrated in FIG. 1A and FIG. 1B. FIG. 1A shows an exemplary graph of the voltage dependence of the steady state of the gating variables for the Ebihara and Johnson current model of the cardiac sodium current. FIG. 1B shows an exemplary graph of the voltage dependence of the time constants of gating variables for the Ebihara and Johnson current model. FIG. 1C shows an exemplary graph of current density vs. generated by the Ebihara and Johnson current model with parameters ($\bar{g}$=23 mS/cm² $\lambda_0$=3, $\lambda_1$=1) and steady state and time constant illustrated in FIG. 1A and 1B respectively. The current model was subjected to voltage clamp stimulations at potentials $u_H$=[−80,−70,−60,−50, −40 ]mV, and $u_T$=10 mV.

Estimation proceeds by first estimating $s_i(u)$ $i \in [0,1]$ with data generated by H-step protocols, and then by estimating $\tau_i(u)$ $i \in [0,1]$ with data gathered by T-step protocols after bounding R=1/$\bar{g}$. Below, we provide a brief description of the procedure in order to facilitate the description of its current limitations, but the interested reader is referred to [20] for detailed descriptions of the inversion procedure.

Estimation of $s_i(u)$ $i \in [0,1]$. Estimation is based on theorems 3.7, 3.1, and 3.8 of Wang and Beaumont [20] below:

$$I_N^{\frac{1}{\lambda_i}}(t, t_r; u, u_T) - 1 = \theta_a \left( -\lambda_i \frac{dI_N(t, tr; u, u_T)}{dt} + J(t = t_r; u, u_T) \right) - \theta_b \int_{t_r}^{t} I_N(t, t_r; u, u_T) dt, \quad (4)$$

$$\frac{s_i(u)}{s_T^{(i)}} = 1 - \frac{J(t; u, u_T) + \lambda_i/\tau_T^{(i)}(1 + \varepsilon_i(t))}{J(t; u, u_T) + \lambda_i/\tau_T^{(i)} + \lambda_i/\tau_T^{(1)}(1 - \varepsilon_i(t))} e^{t/\tau_T^{(i)}}$$

$$\frac{s_i(u)}{s_R^{(i)}} = \left[\frac{I(t; u, u_T)}{I(t; u = u_R, u_T)}\right]^{\frac{1}{\lambda_i}} \left[\frac{J(t; u, u_T) + \frac{\lambda_i}{\tau_T^{(i)}} + \frac{\lambda_{\bar{i}}}{\tau_T^{(\bar{i})}}}{J(t; u_R, u_T) + \frac{\lambda_i}{\tau_T^{(i)}} + \frac{\lambda_{\bar{i}}}{\tau_T^{(\bar{i})}}}\right]^{\frac{\lambda_i}{\lambda_i}} \quad (6)$$

where $t_r$ stands for a reference time in the interval of acquisition, $u_R \in R_H$, $s_\alpha^{(i)}$ stands for $s_i(u_\alpha)$, $\tau_\alpha^{(i)}$ for $\tau_i(u_\alpha)$, $i \in [0,1]$, $\bar{i}$ is the complement of i, $\alpha \in [H,T,R]$, and $$I_N(t, u; t_r, u_T) = \frac{I(t, u; u_T)}{I(t = t_r, u; u_T)}, J(t, u; u_T) = \frac{dI(t, u; u_T)/dt}{I(t, u; u_T)}$$

The functions $\varepsilon_j(t)$, $j \in [0,1]$ are error functions. They become negligible when the conditions of application of the theorems are fulfilled. A test to determine, a-priori from the data, whether the conditions are fulfilled can be found in Wang and Beaumont [20].

A condition of application is data generated by an H-step protocol $u_T > u_H$ for which, $$\{u_T : s_1(u_T) < \varepsilon\}$$

$\varepsilon$: error tolerated [20]. In such condition, $i=0, \bar{i}=1$. Another condition is data generated by an H-step protocol $u_T < u_H$ satisfying $$\{u_T : s_0(u_T) < \varepsilon\}$$

Interestingly, Equations (4)-(6) (theorems 3.7, 3.1, 3.8 [20]) are symmetric, meaning that these equations are still valid for this other condition. The application requires only swapping indices i and $\bar{i}$ of the gating variables.

Estimation proceeds as follows. The parameters $\theta_a, \theta_b$ are obtained applying linear least square fitting to (4). These two parameters are inverted for $\tau_T^{(i)}, \tau_T^{(\bar{i})}$ [20]. Equations (5), (6) are fulfilled for any time on a given current. Thus, the left hand side is estimated averaging the right hand side over all acquisition points of currents recorded at different voltages.

Note that $R_H$ of an H-step protocol with $u_T > u_H$ fulfilling the conditions of application of the theorems has an upper limit. As $u_H \to u_T$, $s_1(u_H) \to s_1(u_T)$ and in an H-step protocol $u_T$ is set such that $s_1(u_T) < \varepsilon$ which is by definition very small. See leftmost panel of FIG. 1. Then from (3) $y_1(t) < \varepsilon$ during the application of the test pulse for $t \in [0, \infty[$. Consequently, in such conditions the current becomes undetectable by the instrumentation. This upper limit is termed: $u_{H0}$. The same applies to an H-step protocol with $u_T < u_H$ fulfilling the conditions of application of the theorems. In this case, there is a lower limit $u_{H1}$ below which the current becomes undetectable by the instrumentation.

Therefore, at least theoretically, $s_i(u)$, $i \in [0, 1]$, $u < u_{H0}$ can be estimated with an H-step protocol for which $u_T > u_H$ and $s_i(u)$, $i \in [0,1]$, $u > u_{H1}$ can be estimated with an H-step protocol for which $u_T < u_H$. Each H-step protocol should fulfill the conditions of application of the theorems.

Estimation of $\tau_i(u)$ $i \in [0,1]$. Theorem 4.1 of Wang and Beaumont [20] stipulates, $$\prod_{i \in A} \gamma_i(y_i; u_H, u_T) = e^{-t_r J(t_r)} \prod_{i \in \bar{A}} \gamma_i(y_i; u_H, u_T) \quad (7)$$

with $$\gamma_i = \begin{cases} \left[\frac{s_T^i - s_H^i}{s_T^i - y_i}\right]^{\frac{\lambda_i(s_T^i - y_i)}{y_i}}, & \text{if } i \in A \\ \left[\frac{s_T^i - s_H^i}{y_i - s_T^i}\right]^{\frac{\lambda_i(y_i - s_T^i)}{y_i}}, & \text{if } i \in \bar{A} \end{cases} \quad (8)$$

for any data point on a current, where A is the set of indices for which sign $ds_i(u)/du = \text{sign}(u_T - u_H)$, and $\bar{A}$ its complement. Note the theorem is applicable to a formalism with multiple gates. However, because we have only two gates, $A=[0], \bar{A}=[1]$ for a T-step protocol with $u_T > u_H$ and vice versa for $u_T < u_H$. Thus, we have $\gamma_i(y_i)$, $y_i \in [s_H^i, s_T^i]$, $i \in [0,1]$, where each $\gamma_i(y_i)$ has only one extremum [20]. The functions $\gamma_i(y_i)$ are employed to systematically find all couples $y_0^{\lambda_0}, y_1^{\lambda_1}$ that can reproduce a data point. From these couples, bounds $R=1/g$ are found. Then pick a values R within the bounds and use (7) to find all gating variables that can reproduce a data point (Algorithm 4.4 in [20]). For each gating variables satisfying condition (7) the time constants are extracted with (3). More details of the inversion can be found in Sect. 4 of [20].

Consider the estimation of $\tau_i(u)$ $i \in [0,1]$ with two complementary T-step protocols, one with $u_T > u_H$ and another one with $u_T < u_H$. In each one $u_H : s_i(u_H) < \varepsilon$ for one of the gating parameters.

This way the current is negligible when the channel is clamped at $u=u_H$. Each protocol is bounded below and above respectively because as $u_T \to u_H$, the current becomes small and cannot be detected by the instrumentation. These bounds are termed $u_{T0}$ and $u_{T1}$. Then at least theoretically $\tau_i(u)$ $i \in [0,1]$ can be estimated with the first and second protocols respectively. Note that in general the two ranges overlap.

Limitations. Several channels, like the sodium channel of nerve, skeletal and cardiac cells, inactivate very rapidly at potentials close to the cell's rest potential. This property is important for tissue excitability because the sodium channel generates a large current during depolarization, but a much smaller one during repolarization, which is essential for the generation of an action potential. As a result, while theorems, 3,7, 3.1, 3.8 and 4.1 of Wang and Beaumont are symmetric [20], currents generated with $u_T$ near the cell rest potential are too small to be reliably detected by the instrumentation. This precludes inverting $s_i(u)$ for $u > u_{H0}$ and $\tau_i(u)$ for $u < u_{T0}$ $i \in [0,1]$.

To alleviate this problem for the estimation of $s_i(u)$ $i \in [0,1]$, a procedure based on a double step protocol was proposed in Wang and Beaumont [20]. The procedure exploits cell memory, i.e., the fact that cell response to stimulation is affected by the potential at which a cell was maintained. The experimentalist had the freedom to set $u_T$ at a value that could generate currents of significant magnitude. While this approach may work for several tissues, it is unfortunately impractical for a number of others. To understand why, one should remember that currents are isolated with pharmacological blockers, meaning that cells have to be stimulated in absence and presence of the blockers. The protocol in question requires maintaining $u_H$ at a large depolarized potential for a long interval of time. Unfortunately, many cells like nerve, skeletal and cardiac cells cannot tolerate a large depolarization for a long interval of time. The cells are simply too leaky at such potentials. The large current flux changes the ionic composition of the intracellular medium and damages the cell. Consequently, protocols requiring $u_H$ to be set at large depolarized potentials are impractical for a number of cell types, including: nerve, skeletal and cardiac cells.

Part 3 Methods

Cordeiro et al. [6] generously provided us access to a voltage clamp data set on the canine sodium current [6]. Below, we briefly describe data acquisition and the pre-processing we performed prior to analysis.

Cell isolation. Adult Mongrel dogs were euthanized and their hearts were excised from their chest. Thin slices of tissue were shaved from the endocardial and epicardial layers of the left ventricular free wall with a dermatome. The tissue slices were immersed in an enzymatic solution for digestion of the collagen. The supernatant was filtered and centrifuged and the pellet containing the myocyte was stored at room temperature [6, 15].

Data acquisition. The currents were recorded with a multiclamp 700 A amplifier from Axon Instruments. The electrode resistance was 1 to 2.5 MΩ. Currents were acquired at 20-50 kHz and filtered at 5 kHz.

To obtain a good voltage control during step stimulation, recordings were made at room temperature and in low extracellular Na solution which was titrated to produce a 5 mV reversal potential. The background potassium current was eliminated with Cesium [6, 15].

The T-step protocol was conducted with $u_H=-120$ mV to recruit all available Na$^+$ channels and $u_T \in [-50,15]$ mV. The H-step protocol was conducted with $u_H \in [-120,-25]$ mV and $u_T=-10$ mV. In each case, data acquisition took place over a minimum of 35 ms. Currents in a total of 15 endocardial and 15 epicardial cells were generated for the H-step protocol as well as for the T-step protocol. From this set we eliminated recordings with a wide capacitive transient because it signifies an unstable membrane, and recordings with poor voltage control. We were left with 8 endocardial and 10 epicardial cells. From the 8 endocardial cells, 2 had invalid T-step recordings.

Pre-processing of the data. The inversion procedure uses the time derivative of the current, which could be inaccurate on noisy current. Thus, prior to any processing the acquired data was filtered using a moving average filter with a mask 10 data points wide.

The mask width was picked large enough to eliminate, on the derivative of the smoothed trace, all peaks produced by noise on the data, still have a curve that runs smoothly within the noise. This was found by trial and error. This choice of mask width can vary for each data set, but is relatively easy to find because the noise is at a much higher frequency that any change in time on the current.

Figure 2:
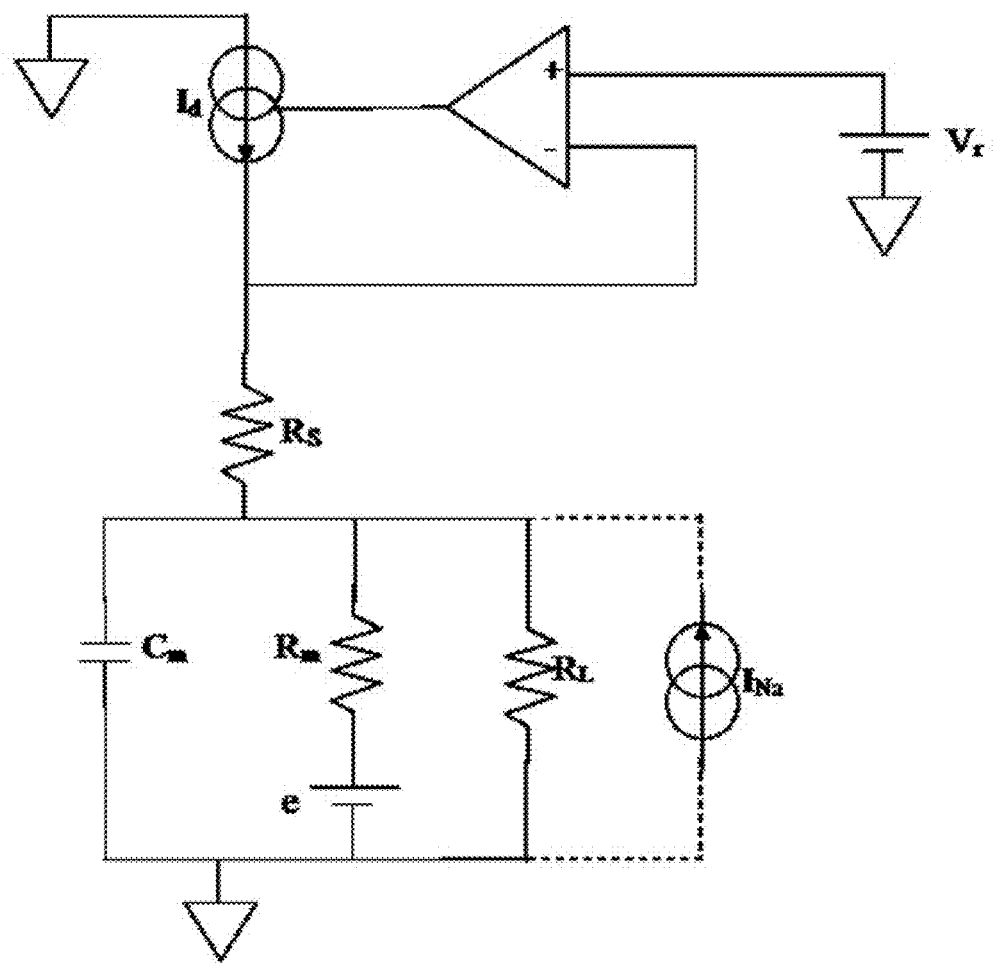
FIG. 2 shows an exemplary equivalent electrical circuit for voltage control and current recordings.

To subtract the capacitive transient from the total current in a manner to extract the ionic current, we represented the cell-pipette configuration with the equivalent electric circuit illustrated in FIG. 2. where $I_d$: Total recorded current, $I_{Na}$ Sodium current, $V_r$: Reference voltage, $R_s$: Series resistance, $C_m$: Membrane capacitance, $R_m$: Membrane resistance, e: Reversal Potential, $R_L$: Leak resistance.

In this representation the membrane is represent by a resistor capacitor element. We fit (here the fit is linear with all parameters except one) the circuit equation to the experimental data. Then obtain the value of the membrane capacitance from the equation which allows us to subtract the capacitive transient analytically. The circuit equation is given by:

$$I_d(t) = a_0 e^{-i\alpha} + a_1, \quad (9)$$

-continued $$\alpha = -\frac{R_L R_m + R_S R_m + R_S R_L}{C_m R_S R_m R_L},$$

$$a_0 = a_1 + \frac{u_T - u_H}{R_S},$$

$$a_1 = \frac{V_r(R_m R_L) - e R_L}{-R_L R_m + R_S R_m + R_S R_L}$$

(9) was fitted to the first 0.1 and last 8 ms of the data acquired over 35 ms because $I_{Na}$ is negligible in this interval. Specifically it is not activated and fully inactivated. The parameter estimation was performed as follows: for a given α, $a_0$, and $a_1$ were estimated through linear least square fitting. The parameter α was varied from −30 to −4 taking 1,000 samples. The optimal α, $a_0$, and $a_1$, are the ones minimizing the residual of (9). Note, that the fit for each current was performed because the capacitive transient is quite sensitive to $R_L$, and this parameter may change from one recording to another because the pipette may slightly move during acquisition The circuit equation is given by:

Subsequently, a weighted average of the currents was performed with respect to cell size. To approximate cell size a linear relationship between the peak current magnitude recorded at a specific voltage of a T-step protocol was assumed. For that protocol the smallest and largest peak currents were 2 and 8 nA, which corresponds to a ratio of 4 in cell size.

Figure 3:
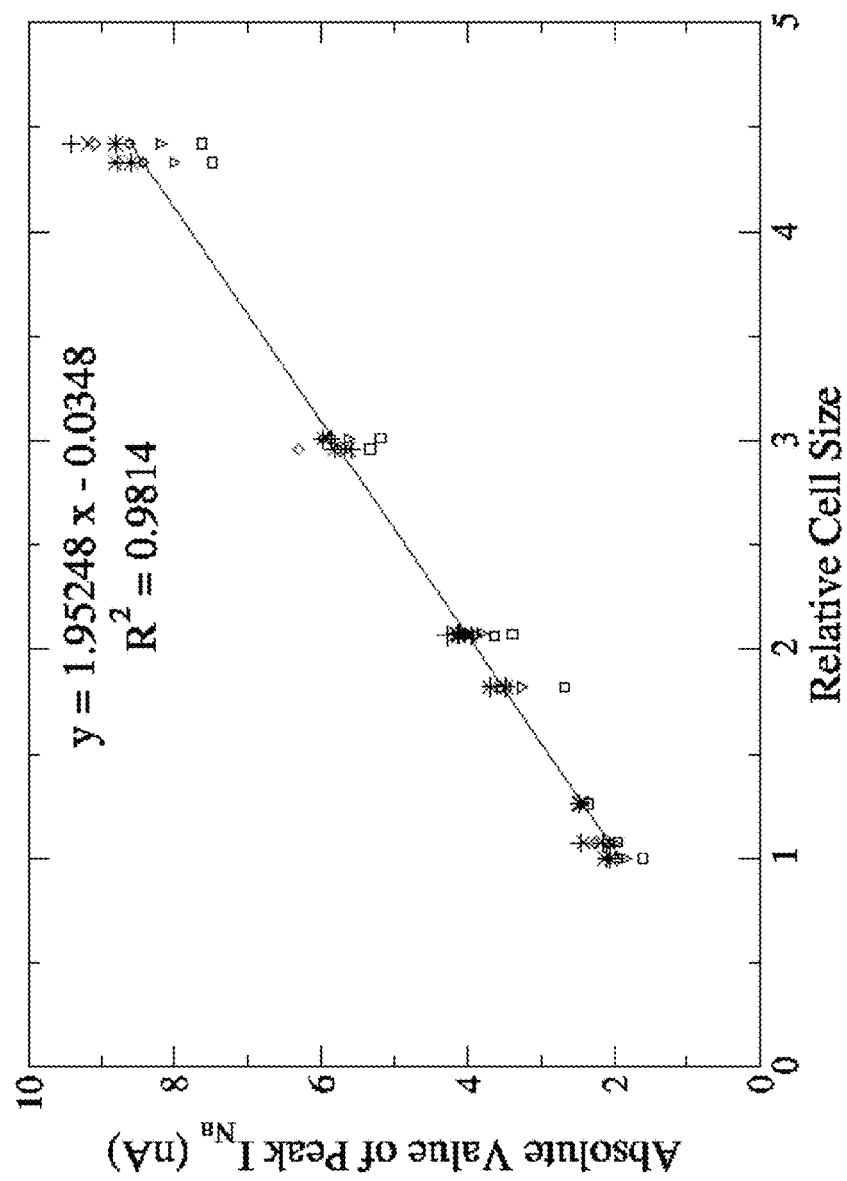
FIG. 3 shows an exemplary graph of absolute value of peak current vs. relative cell size.

The size of the other cells of this group, abcissa in FIG. 3, were evaluated based on their peak current magnitude using this linear relation. FIG. 3 shows an exemplary graph of absolute value of peak current vs. relative cell size, illustrating the linear relationship between peak currents amplitude and cell size (solid line) deduced from peak currents recorded at a specific reference voltage of a T-step protocol in epicardial cells. Each symbol is the rescaled peak current in the same protocol but recorded at another voltage. The scaling factor, one number for each voltage other than the reference voltage, normalizes the current in the smallest cell to 2 nA, the first point on the curve. Then the peak currents in the same group of cells but measured at different potentials are scaled and placed on the graph, thus size and peak are known for these points. The scaling factor, only one number for all cells, is found by making the peak current of the smallest cell to match the first point on the graph, i.e. 2 nA. All peak currents follow the same linear trend with a correlation coefficient of 0.9814.

Figure 4A:
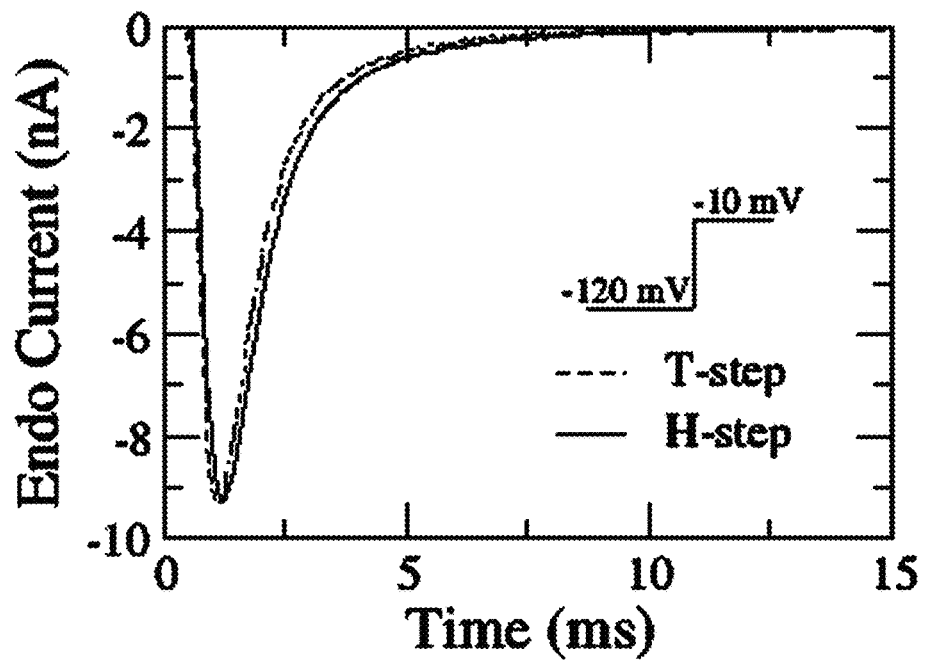
FIG. 4A shows an exemplary graph of endocardial layer cell current vs. time.
Figure 4B:
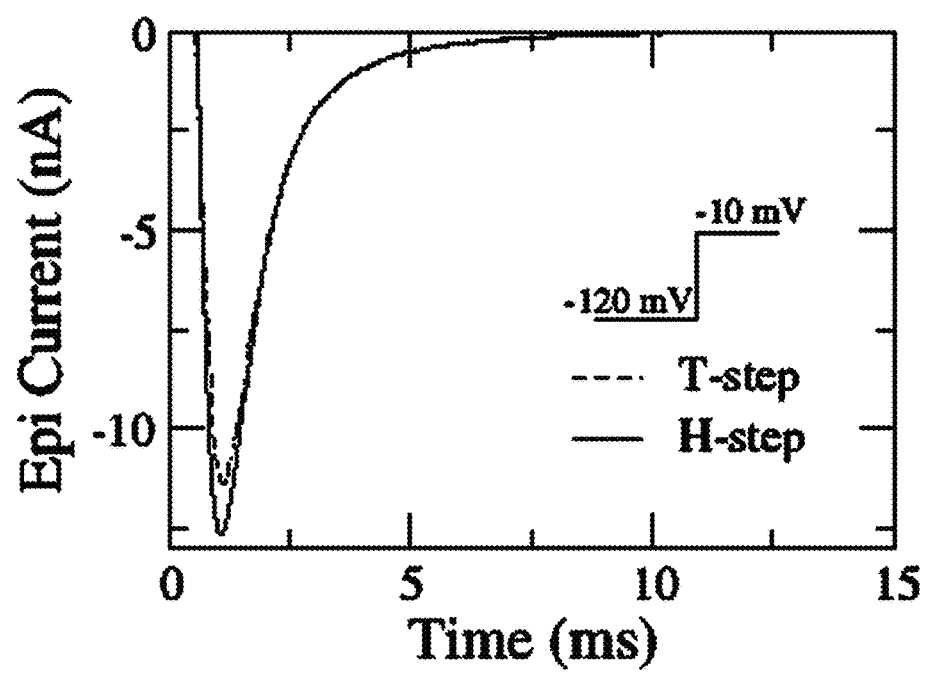
FIG. 4B shows an exemplary graph of epicardial layer cell current vs. time.
Figure 5B:
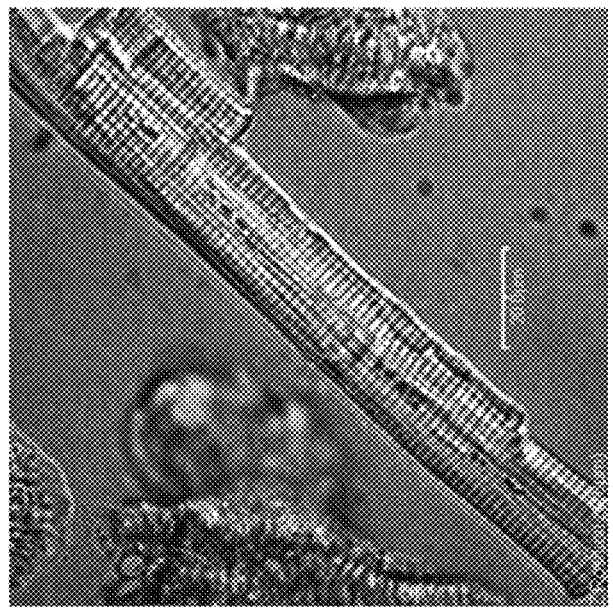
FIG. 5B shows another exemplary photomicrograph of cells isolated from the epicardial layer.
Figure 5A:
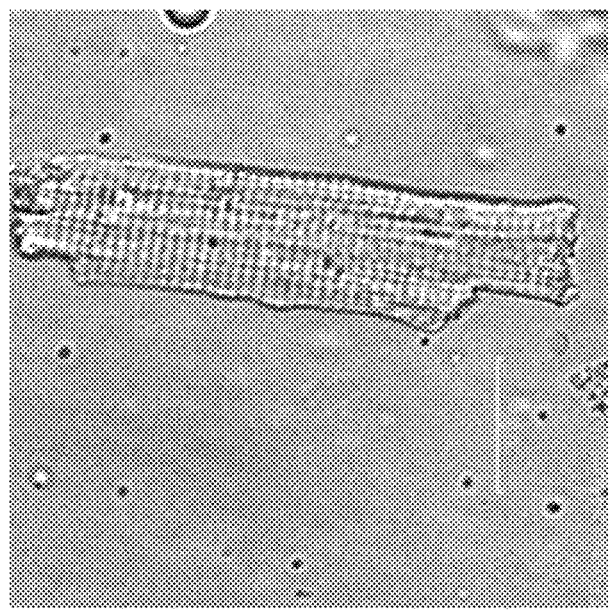
FIG. 5A shows an exemplary photomicrograph of cells isolated from the epicardial layer.
Figure 6A:
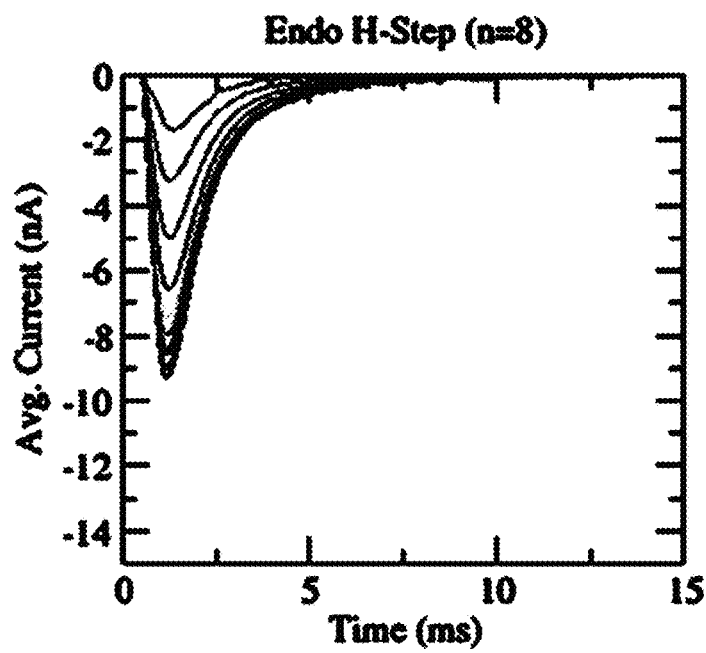
FIG. 6A shows an exemplary graph of average endocardial cell current vs. time for an H-Step stimulation protocol (n=8)
Figure 6B:
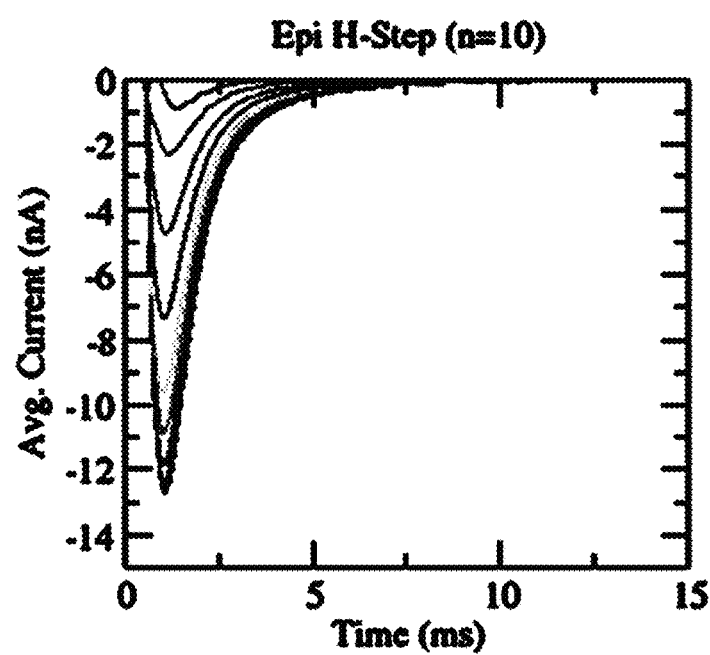
FIG. 6B shows an exemplary graph of average epicardial cell current vs. time for an H-Step stimulation protocol (n=8)
Figure 6C:
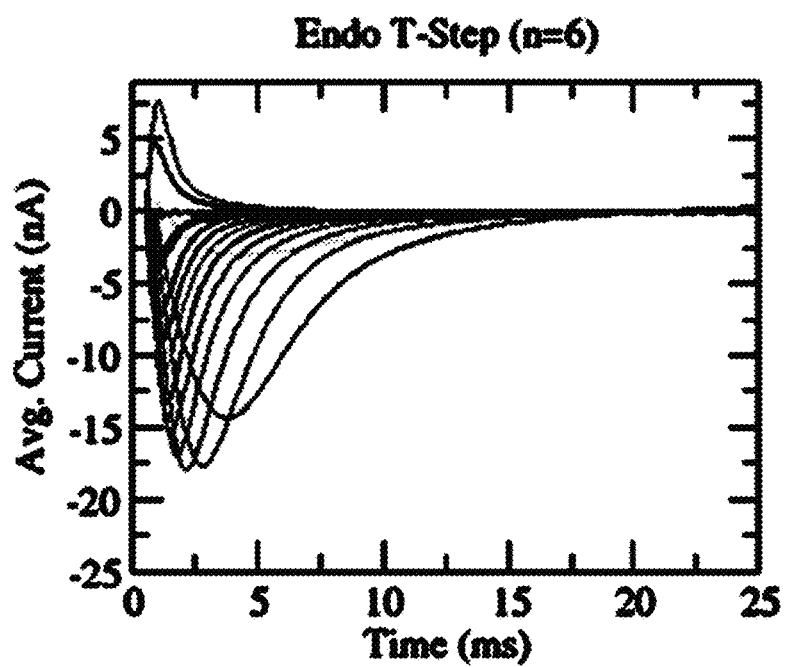
FIG. 6C shows an exemplary graph of average endocardial cell current vs. time for an T-Step stimulation protocol (n=6)
Figure 6D:
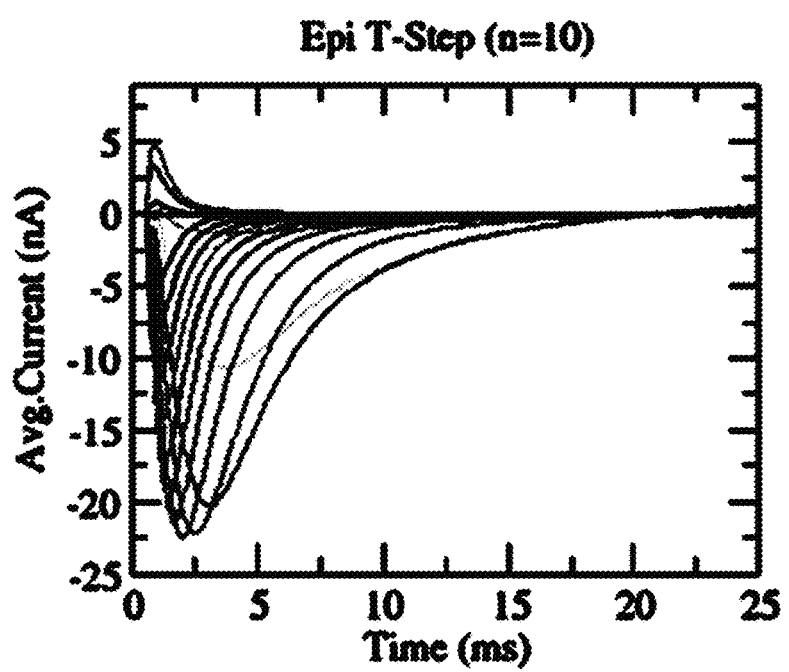
FIG. 6D shows an exemplary graph of average epicardial cell current vs. time for an T-Step stimulation protocol (n=10)

FIG. 4A shows an exemplary graph of endocardial cell current vs. time, and FIG. 4B shows an exemplary graph of epicardial cell current vs. time. FIG. 4A and FIG. 4B show currents during data acquisition with H-step and T-step protocols with voltages $u_H=-120$ mV and $u_T=-10$ mV FIG. 5A shows an exemplary photomicrograph of cells isolated from the epicardial layer. FIG. 5B shows another exemplary photomicrograph of cells isolated from the epicardial layer of the heart. FIG. 5A and FIG. 5B show examples of difference in size of cells isolated from the heart.

Finally FIG. 6 shows the resulting weighted average for cell size of sodium currents gathered in endocardial and epicardial cells with H-step and T-step protocols. FIG. 6A, FIG. 6B, FIG. 6C, and FIG. 6D show averaged currents of the H-step and T-step protocols for endocardial and epicardial cells after preprocessing of the raw data provided by [6]. Currents shown from the T-step protocol are conducted with $u_H=-120$ mV and $u_T \in [-50,15]$ mV by 5 mV increment. The H-step protocol was conducted with $u_H \in [-120,-25]$ mV by 5 mV increment and $u_T=-10$ mV. In the titles, n indicates the number of cells averaged. FIG. 6A shows an exemplary graph of average current vs. time for an endo H-Step (n=8). FIG. 6B shows an exemplary graph of average current vs. time for an epi H-Step (n=8). FIG. 6C shows an exemplary graph of average current vs. time for an endo T-Step (n=6). FIG. 6D shows an exemplary graph of average current vs. time for an epi T-Step (n=10).

Part 4 Results 4.1 Application to an Incomplete Biological Data Set

Figure 7:
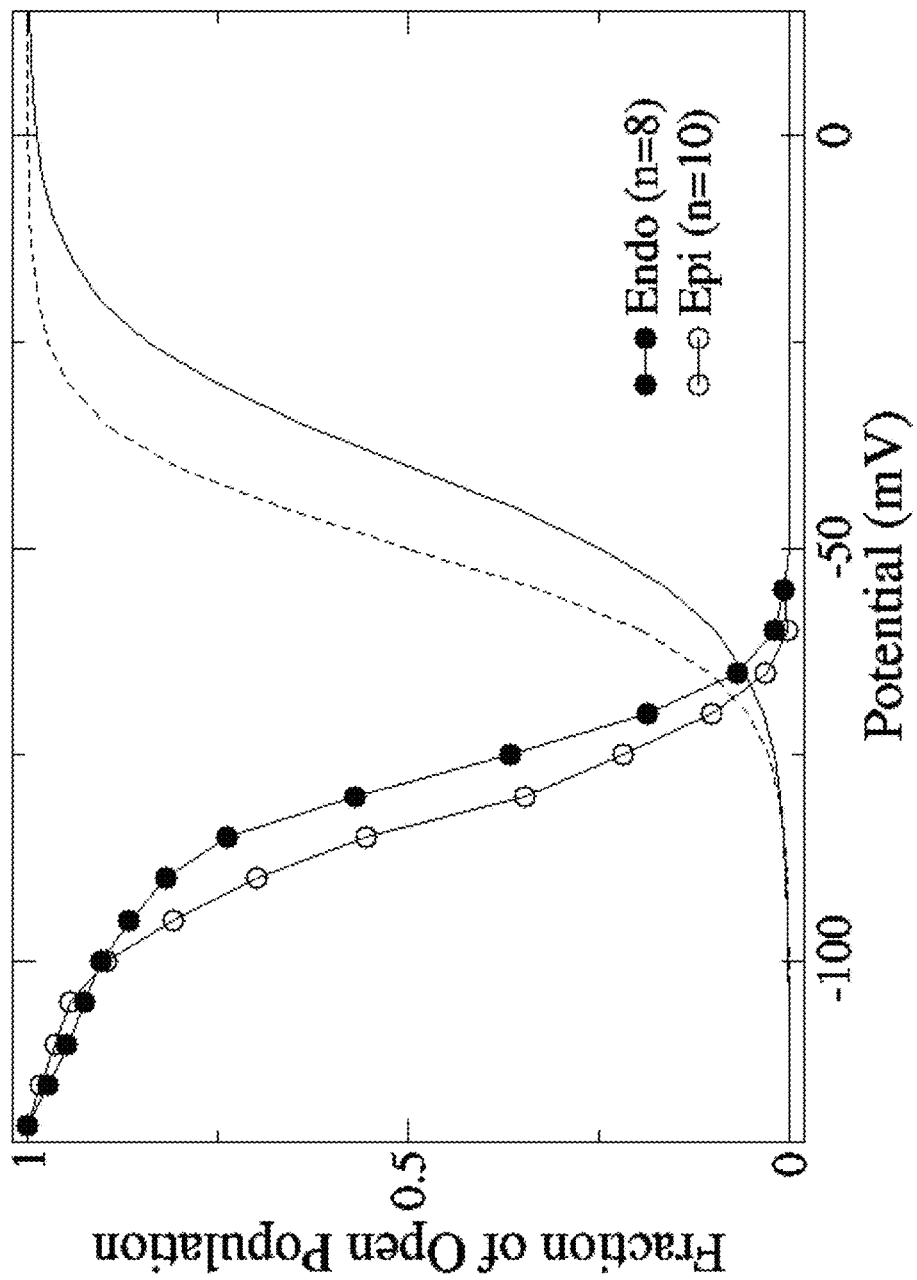
FIG. 7 shows an exemplary graph of the voltage dependence of the steady state vs. potential for endocardial (n=8) and epicardial (n=10) cells.

The inversion procedure was applied to the Biological data described in the previous section. As mentioned in Part 2, estimation was performed with various combinations of $\lambda_i$, $i \in [0,1]$. It was found that $\lambda_0=4$ and $\lambda_1=1$ gave the best results, a larger invertible range capable of reproducing the data, and this result is reported. The results reported in FIGS. 6-9, illustrate the superiority of our method since we were able to find two different Hodgkin-Huxley formalism that could reproduce equally well the experimental data. This is a rather unexpected result since the data set at the basis of the estimation is quite extensive, and based on current knowledge an expert in the field would assume the data set fully constrain the model. Showing that it is not the case is a significant accomplishment. Estimation of $s_i(u)$ $i \in [0,1]$. As described in Part 2, the functions $s_i(u)$, were obtained with theorems 3.7, 3.1 and 3.8 of Wang and Beaumont [20] and based on data generated with the H-step protocol. Because the voltage from which the maximal current was elicited for each H-step protocol were slightly below −50 mV, as shown in FIG. 7 $s_i(u)$ $i \in [0,1]$ was estimated up to this voltage. FIG. 7 shows an exemplary graph of the voltage dependence of the steady state of the gating variables for endocardial (n=8) and epicardial (n-10),. Values found through inversion are marked with circles. The solid lines on these curves (curves with symbol) are just interpolation. Note that $s_i(u)$ as reported herein is different from the channel availability curve reported by Cordeiro et al. [6]. The latter constitutes a well-accepted measure of channel availability in electrophysiology and has no trivial relation to $s_i(u)$.

Based on the inversion procedure, the data of FIG. 6, does not specify steady state activation $s_0(u)$. It specifies only steady state inactivation $s_i(u)$. Therefore to complete the inversion we assumed arbitrarily the voltage dependence of two different steady state activation $s_0(u)$. They are illustrated with solid and broken lines in FIG. 7 (curves on the right). Then performed the inversion with each of these different steady state activation.

Estimation of $\tau_i(u)$ $i \in [0,1]$. As mentioned in Part 2 and described in a more detailed manner in Part 4 of [20], estimation of $\tau_i(u)$ includes to first bound R, and then extract time constants corresponding to a value of R picked within the bounds. If the data constrain the estimation problem the bounds are narrow. In the specific inversion performed in this section of the manuscript, 10% of noise on the current. The results are shown in FIG. 8A, FIG. 8B, FIG. 8C, FIG. 8D, FIG. 9A, FIG. 9B, FIG. 9C, and FIG. 9D. The estimation was repeated using the two different $s_0(u)$ of FIG. 7 (solid and broken lines). As explained in Part 2, and described in a detailed manner in [20], the procedure includes to first bound R=1/g. Then a $\tau_i(u)$, $i \in [0,1]$, that can reproduce the data can be found for each R picked within the bounds. The extraction procedure follows: Once R is fixed we find all couples of gating variables $y_i$ that can reproduce the data within a given error tolerance. Then because the steady state is known at each voltage of the stimulation, the time constants can be extracted from (3). The inversion of the functions $\gamma_i(y_i)$ is used to find in a systematic manner all couples $y_i$ that reproduce the data within a given error tolerance. Part 2 (hereinabove) and Wang and Beaumont [20] describe more details of the procedure.

Figure 8A:
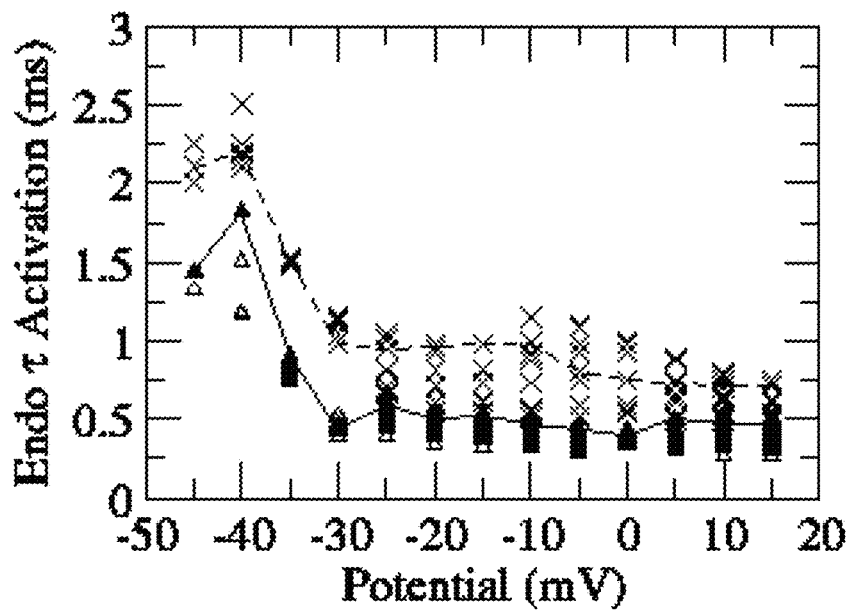
FIG. 8A shows an exemplary graph of the voltage dependence of the time constant of the activation gating variable for endocardial cells, estimated with data generated by the T-step stimulation protocol (n=8)
Figure 8B:
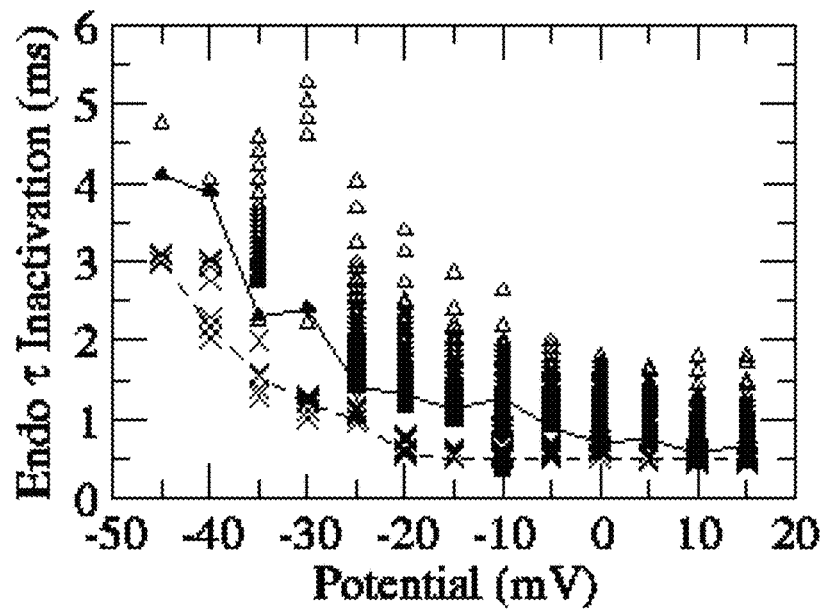
FIG. 8B shows an exemplary graph of the voltage dependence of the time constant of the inactivation gating variable for endocardial, T-step stimulation protocol (n=10)
Figure 8C:
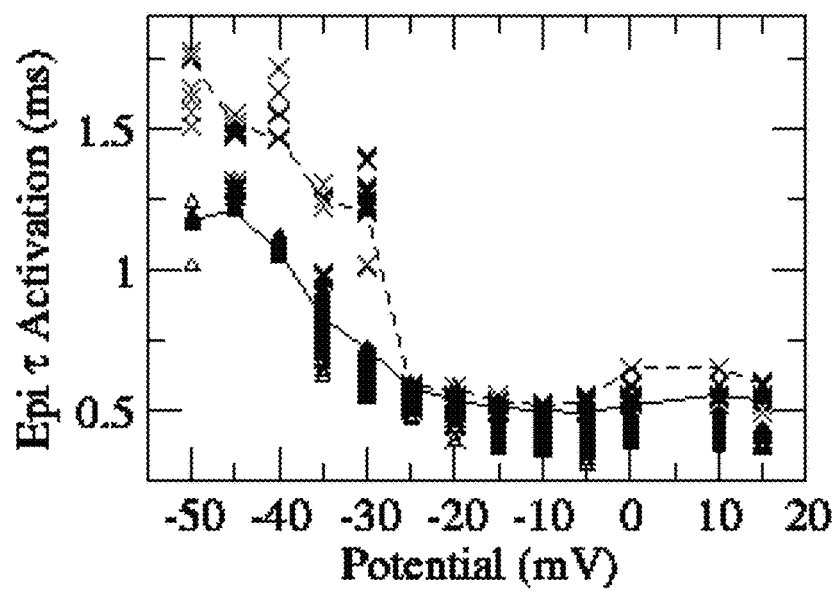
FIG. 8C shows an exemplary graph of the voltage dependence of the time constant of the activation gating variable for endocardial cells, estimated with data generated by the T-step stimulation protocol (n=6)
Figure 8D:
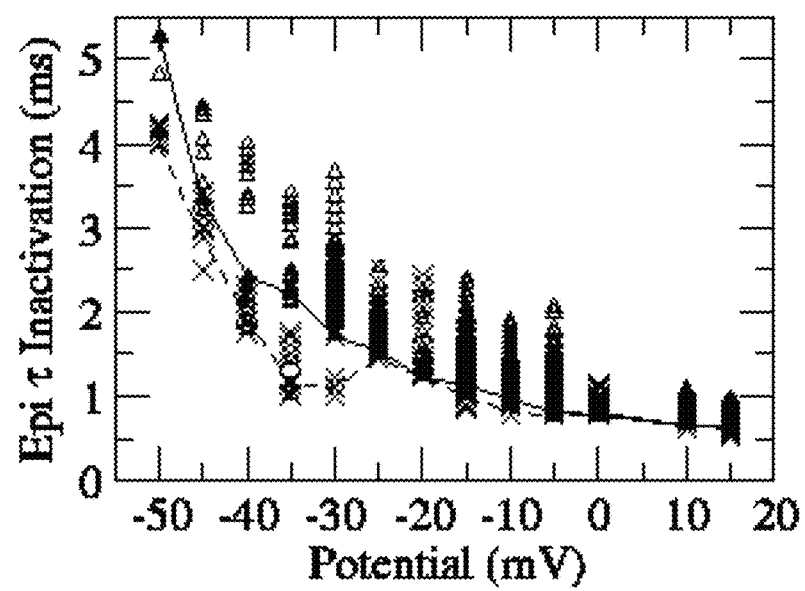
FIG. 8D shows an exemplary graph of the voltage dependence of the time constant of the inactivation gating variable for epicardial, T-step stimulation protocol (n=10)

FIG. 8A, FIG. 8B, FIG. 8C, FIG. 8D show the voltage dependence of $\tau_i(u)$ extracted with the inversion procedure and using two different sets of gating parameters, the difference being in $s_0(u)$ corresponding to the solid and broken lines in FIG. 7A, FIG. 7B. The functions $s_0(u)$ empoyed were the ones illustrated in FIG. 7A, FIG. 7B: They were used for the estimation with both the endocardial and eicardial data. Solid lines and triangles in FIG. 8A, FIG. 8B were extracted using $s_0(u)$ corresponding to the solid line with R=0.0333 and R=0.0526 for endocardial and epicardial data respectively. Dashed line and Xs were extracted using $s_0(u)$ corresponding to the dashed line with R=0.4662 and R=0.0968 for endocardial and epicardial data respectively. The symbols illustrate the range of time constants, and the lines a time constant corresponding to a specific value of R. FIG. 8A shows a graph of activation time constant vs. potential for endocardial cells, T-step (n=8). FIG. 8B shows a graph of inactivation time constant vs. time for endocardial cells, T-step (n=10). FIG. 8C shows a graph of current vs. activation time for epicardial cells, T-step (n=6). And, FIG. 8D shows a graph of activation time constant vs. time for epicardial cells, T-step (n=10). The inversion was performed for the two different $s_0(u)$ shown in FIG. 7. Specifically the bounds on R were quite similar when the two different $s_0(u)$ were used in the inversion. They were [0.03, 0.048] for the endocardial data and [0.048,0.101] for the endocardial data. The time constants for the endocardial data were extracted with R=0.0333 using $s_0(u)$ corresponding to the solid line in FIGS. 7, and R=0.4662 for $s_0(u)$ corresponding to the broken line. Similarly for the epicardial data we picked R=0.0526 and R=0.0968 when $s_0(u)$ corresponded to the solid and broken lines in FIG. 7. Clearly the functions of voltage extracted are quite different from one another.

Figure 9A:
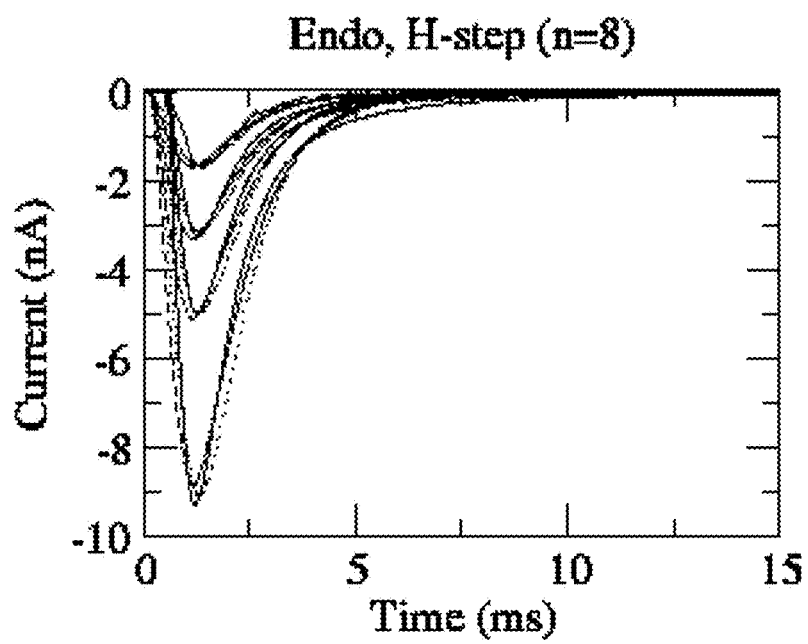
FIG. 9A shows an exemplary graph of current vs. time recorded in an endocardial cell subjected to the H-step stimulation protocol.
Figure 9B:
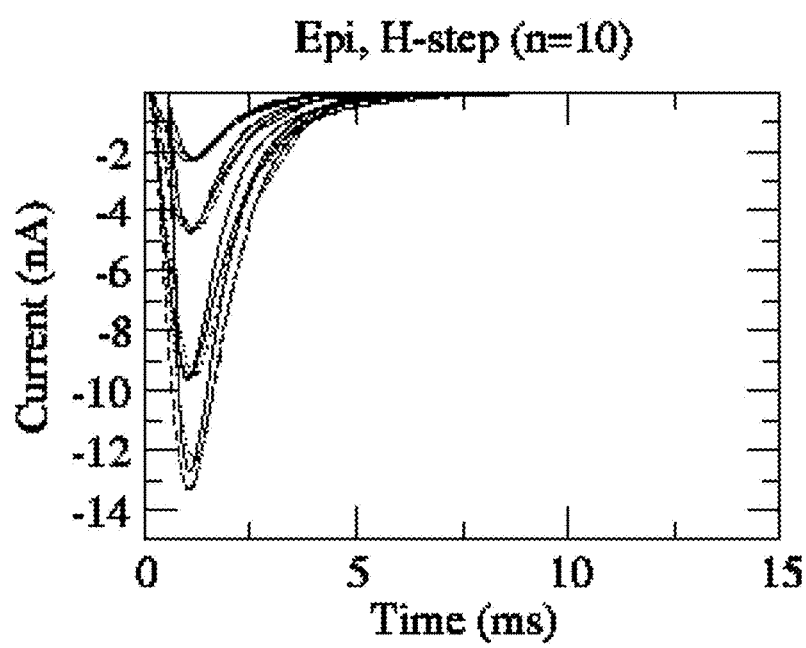
FIG. 9B shows an exemplary graph of current vs. time recorded in an epicardial cell subjected to the H-step stimulation protocol.
Figure 9C:
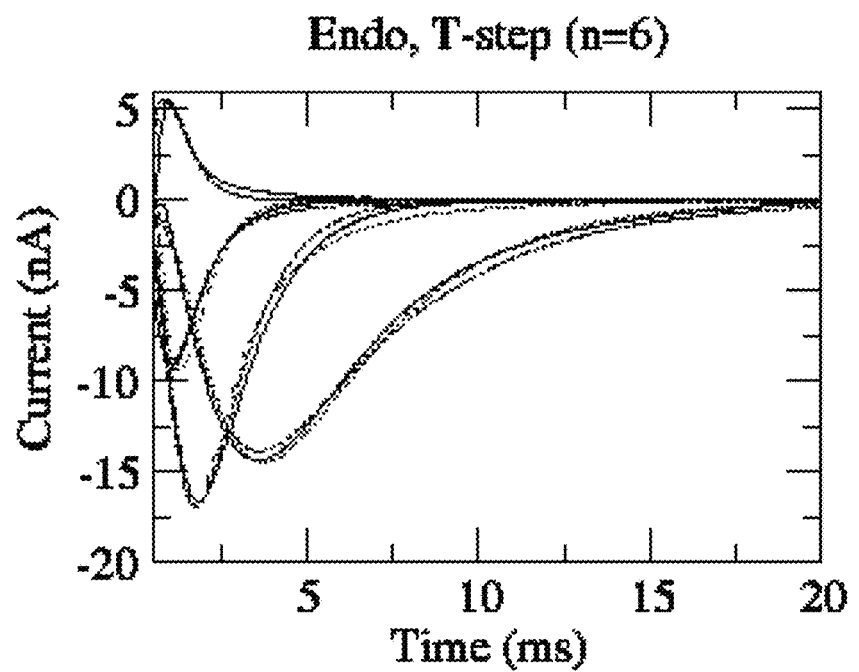
FIG. 9C shows another exemplary graph of current vs. time recorded in an endocardial cell subjected to the T-step stimulation protocol.
Figure 9D:
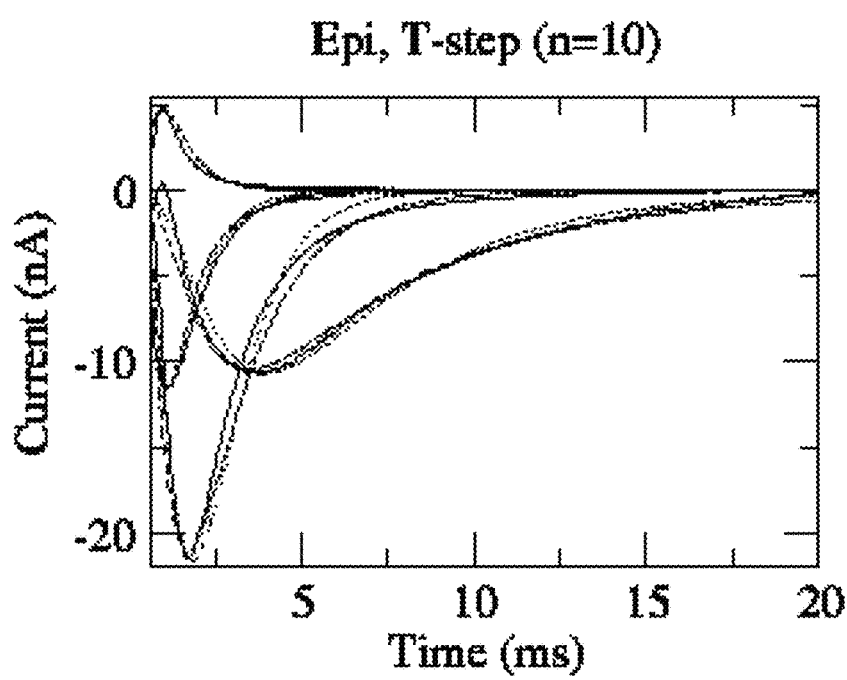
FIG. 9D shows an exemplary graph of current vs. time recorded in an epicardial cell subjected to the T-step stimulation protocol.

Still as shown in FIG. 9A, FIG. 9B, FIG. 9C, and FIG. 9D, each model reproduces the data within the pre-specified error tolerance. The figure compares the experimental data with the currents generated with the different current model (3 curves for each voltage). FIG. 9A shows a graph of current vs. time generated wtih the H-step protocol applied endocardial cells. FIG. 9B shows a graph of current vs. time generated with the H-step protocol applied to epicardial cells. FIG. 9C shows another graph of current vs. time generated with the the T-step protocol applied to endocardial cells. FIG. 9D shows a graph of current vs. time generated with the T-step protocol applied to epicardial cells. Each current are for the experimental data, and the two different models (differ by steady state activation). Note that other time constants could have been extracted by picking other values of R within the bounds. This would have generated functions of voltage running through the space delimited by the symbols in the graphs. These functions should be extracted using the inversion procedure. We have not generated such $\tau_i(u)$ with other values of R here, but are illustrating this possibility in Part 4.3, on the effect of noise on the data.

In summary, FIG. 7, FIG. 8A, FIG. 8B, FIG. 8C, FIG. 8D, and FIG. 9A, FIG. 9B, FIG. 9C, and FIG. 9D clearly illustrate that quite different models if estimated with data exclusively generated with the H-step and T-step protocol an reproduce a relatively extensive data set, and this irrespective of the number of data points and potentials sampled in the range of each stimulation protocol. So the data set, does not constrain the estimation problem, i.e., we say it is incomplete.

4.2 Application to a Complete Synthetic Data Set

Estimation of $s_i(u)$, $i \in [0,1]$. To overcome the limitation raised in Part 2, we add voltage clamp data to the conventional data set and introduce new processing. The voltage clamp data were generated with the Ebihara and Johnson sodium current model [7].

Figure 10A:
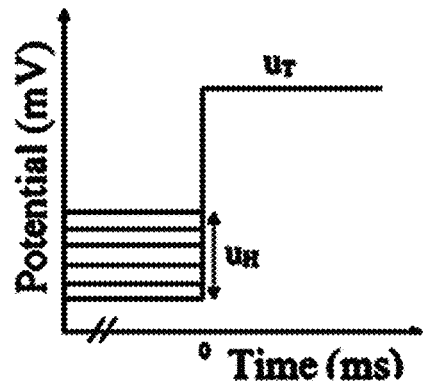
FIG. 10A shows an exemplary graph of potential vs. time illustrating the H-step voltage clamp stimulation protocol.
Figure 10B:
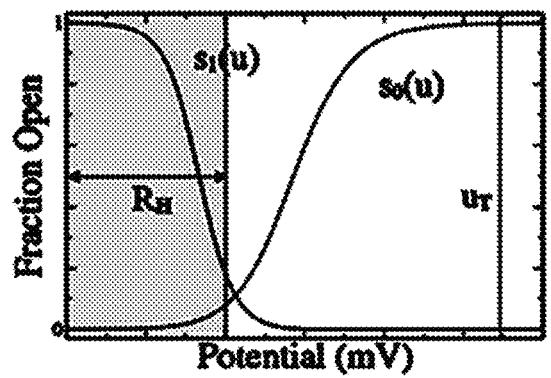
FIG. 10B shows an exemplary graph of the steady state of the gating variables vs. potential over the voltage range where the steady states can be estimated with data generated by the protocol of FIG. 10A (H-step)
Figure 10C:
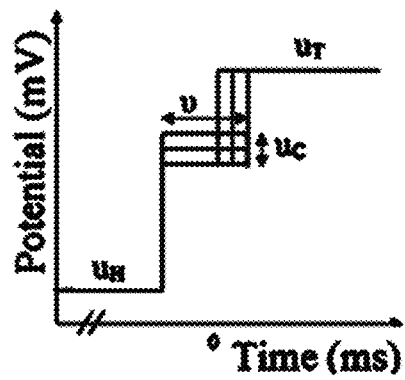
FIG. 10C shows an exemplary graph of potential vs. time illustrating the C-step voltage clamp stimulation protocol.
Figure 10D:
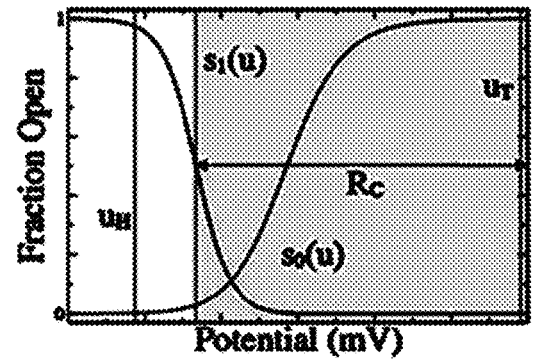
FIG. 10D shows an exemplary graph of the steady state of the gating variables vs. potential over the voltage range where the steady state can be estimated with data generated by the protocol of FIG. 10C (C-step)
Figure 10E:
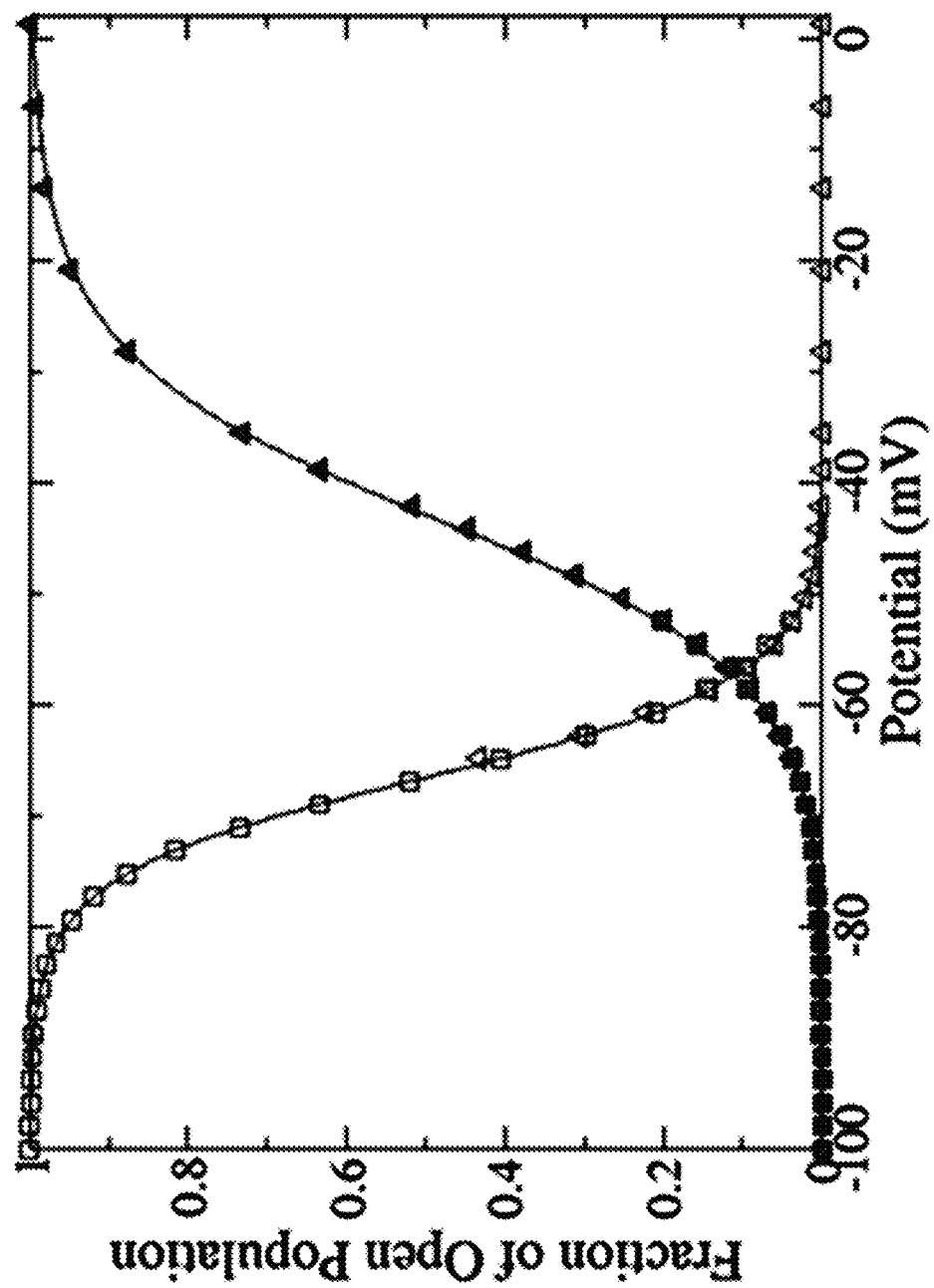
FIG. 10E shows an exemplary graph of the voltage dependence of the steady state of the gating variables for estimation with protocols of the protocols of FIG. 10A and FIG. 10C.

The additional voltage clamp data are generated subjecting the Ebihara and Johnson current model to a new stimulation protocol, termed the C-step protocol, the purpose of which is to probe $s_i(u)$ $i \in [0,1]$ at large depolarized potentials. FIG. 10A shows an exemplary graph of potential vs. time illustrating a voltage clamp stimulation protocol. FIG. 10B shows an exemplary graph of the voltage dependence of the steady state The shaded area indicates the range of voltage by where inversion can recover steady state from data generated with the protocol of FIG. 10A. FIG. 10C shows an exemplary graph of potential vs. time illustrating a new voltage clamp stimulation protocol, the C-step protocol. FIG. 10D shows an exemplary graph of the voltage dependence of the steady state of the gating variable. The shaded are indicated the range of potential where inversion can recover steady state from data generated with the protocol of FIG. 10C. FIG. 10E shows an exemplary graph of the voltage dependence of the steady state of the gating variables, illustrating (symbols) the results of the estimation with protocols of the protocols of FIG. 10A and FIG. 10C superimposed to the original model steady states. In FIG. 10E: the results of the estimation with protocols of panels FIG. 10A (squares) and panel FIG. 10C (triangles) are superimposed to the steady states.

In the new protocol of FIG. 10C, a conditioning pulse is inserted between the holding and test potentials. Currents are interpreted during the application of the test pulse. The conditioning pulse voltage is chosen in a manner to probe $s_i(u)$, $i \in [0,1]$ in the desired voltage range, and its duration in a manner to generate independent currents, as tested using the conditions in Part 2, in the monitoring interval. This duration can be chosen iteratively with the data collection, because each data set will can be tested for independence before application of the method. To start, durations are chosen in the same magnitude of the time constant, which can be approximated from the time course of the data. The range of the stimulation protocol is denoted by $R_C$. The stimulation overcomes the limitations discussed in Part 2, because $u_H$ is never held at a large depolarized potential for a long interval of time, and the experimentalist has the freedom to set $u_T$ to a value that generates a large current as long as $\{u_T : s_1(u_T) < \varepsilon\}$. FIG. 11A and FIG. 11B show the current produced with this protocol for sodium. FIG. 11A show a graph of current vs. time for a duration of 0.2 ms. FIG. 11B show a graph of current vs. time for a duration of 0.4 ms. Currents generated by the Ebihara and Johnson model [7] are subjected to the C-step stimulation protocol of FIG. 10C. The protocol has parameters $u_H = -120$ mV, $u_T = -10$ mV, $u_C \in [-55, 0]$ every 5 mV. The conditioning pulse durations were 0.2 ms (left) and 0.4 ms (right).

The value of the gating variables at the end of the conditioning pulses of duration is denoted as $v_a$ or $v_b$, $v_a < v_b$ by $y_C^{(i)}(v_k)$ $k \in [a,b]$, and a new expression relating $y_C^{(i)}(v_k)$, $s_C^{(i)}$, $i \in [0,1]$, $k \in [a,b]$ isolating $e^{-1/\tau_T^{(i)}}$ is obtained from (3)

$$\left[\frac{y_C^{(i)}(v_a) - s_C^{(i)}}{s_H^{(i)} - s_C^{(i)}}\right]^{\frac{1}{v_a}} = \left[\frac{y_C^{(i)}(v_b) - s_C^{(i)}}{s_H^{(i)} - s_C^{(i)}}\right]^{\frac{1}{v_b}}, i \in [0,1] \quad (10)$$

$y_C^{(i)}(v_k)$ is evaluated from currents recorded during the application of the test pulse in the C-step protocol (FIG. 10), then solved (10) for $s_C^{(i)}$, for each conditioning voltage of the C-step protocol. If the kinetic data can be represented by a Hodgkin-Huxley formalism, condition 1 is expected to be fulfilled Condition 1

$$y_C^0(v_b) > y_C^0(v_a) > s_H^0 \text{ and}$$

$$y_C^1(v_b) < y_C^1(v_a) < s_H^1 \quad \text{(Lemma 1)}$$

Condition 1 can be tested a-priori, because $s^i(u)$ and $y_i(t)$, $i \in [0,1]$ are monotonic, Lemma 1 applies and allows us to unambiguously estimate $s_C^i$ satisfying (10). If condition 1 is not satisfied, it can be concluded that the kinetic data cannot be represented by a Hodgkin-Huxley formalism If condition 1 is fulfilled, for given $y_C^i(v_k)$, $i \in [0,1]$, $k \in [a,b]$, the objective functions $$\Theta_i(s_C^i) = h_a^i(s_C^i) - h_b^i(s_C^i), h_k^i(s_C^i) = \left[\frac{s_C^i - y_C^i(v_k)}{s_C^i - s_H^i}\right]^{\frac{1}{v_k}} \quad (11)$$

have at most one zero if, $$\frac{v_a}{v_b}\left[\frac{y_C^i(v_a) - s_H^i}{y_C^i(v_b) - s_H^i}\right] < 1 \quad (12)$$

and at most two zeros if otherwise. Specifically $$\Theta_0(\xi) \text{ has } \begin{cases} \text{at most one zero if} & h_a^0(\xi=1) < h_b^0(\xi=1) \\ \text{at most two zeros if} & h_a^0(\xi=1) > h_b^0(\xi=1) \end{cases}$$

$$\Theta_1(\xi) \text{ has } \begin{cases} \text{at most one zero if} & h_a^1(\xi=0) < h_b^1(\xi=0) \\ \text{at most two zeros if} & h_a^1(\xi=0) > h_b^1(\xi=0) \end{cases}$$

Proof Consider $\Theta_0(\xi)$. Because $s_0(u)$ and $y_0(t)$ are monotonically increasing functions of u and t respectively, and $v_a < v_b$ (imposed by the C-step protocol), $$0 < s_H^0 < y_C^0(v_a) < y_C^0(v_b) < s_C^0 < s_T^0 < 1. \quad (13)$$

Consequently the domain of each $h_k^0(\xi)$, are $$h_a^0(\xi), \xi \in [y_C^0(v_a), 1] \quad h_b^0(\xi), \xi \in [y_C^0(v_b), 1]$$

Note that each $h_k^0(\xi)$ is a monotonically increasing function of $\xi$ and due to (13), the numerator and denominator of each function are non-null and have the same sign. At the lower bound, $\xi = y_C^0(v_b)$, of the interval where we are seeking the intersection, $$h_b^0(\xi = y_C^0(v_b)) = 0 < h_a^0(\xi = y_C^0(v_b))$$

Therefore a solution exists if $h_k^0(\xi)$ intersect at least once. Furthermore at the first intersection we should have, $$\left.\frac{\partial h_b^0(\xi)}{\partial \xi}\right|_{\xi=\xi^*} \geq \left.\frac{\partial h_a^0(\xi)}{\partial \xi}\right|_{\xi=\xi^*} \quad (14)$$

$\xi^*$ being the coordinate of the intersection. Taking the derivative of $h_k^0(\xi)$ with respect to $\xi$ and eliminating similar terms at $\xi = \xi^*$, the above condition becomes, $$\frac{1}{v_b}\left[\frac{y_C^0(v_b) - s_H^0}{\xi^\Sigma - y_C^0(v_b)}\right] \geq \frac{1}{v_a}\left[\frac{y_C^0(v_a) - s_H^0}{\xi^\Sigma - y_C^0(v_a)}\right], \quad (15)$$

Rearranging to regroup the terms depending on $\xi^\Sigma$ on the left hand side, $$f(\xi^\Sigma) = \left[\frac{\xi^\Sigma - y_C^0(v_a)}{\xi^\Sigma - y_C^0(v_b)}\right] \geq \frac{v_b}{v_a}\rho, \quad \rho = \left[\frac{y_C^0(v_a) - s_H^0}{y_C^0(v_b) - s_H^0}\right] \quad (16)$$

which is permitted because the numerator and denominator of each side of (15) are nonnull and have the same sign.

Remark that $$\frac{df(\xi^\Sigma)}{d\xi^\Sigma} < 0 \quad (17)$$

with asymptotes at $\xi^\Sigma = y_C^0(v_b)$ and $f(\xi^\Sigma) = 1$. Then if $((v_b/v_a)\rho) < 1$, $$f(\xi^\Sigma = \xi^{\Sigma\Sigma}) = (v_b/v_a)\rho, \quad (18)$$

$$\xi^{\Sigma\Sigma} = \frac{y_C^0(v_a) - y_C^0(v_b)(v_b/v_a)\rho}{1 - (v_b/v_a)\rho} < y_C^0(v_a)$$

Due to the fact that $\xi^{\Sigma\Sigma} < y_C^0(v_a)$ inequality (14) is respected in $\xi^\Sigma \in [y_C^0(v_b), 1]$. Because the inequality does not change within this interval, the number of intersections between $h_k^0(\xi)$ is limited to at most one if $(v_b/v_a)\rho > 1$, and $\xi^{\Sigma\Sigma} > 1$, then the number of intersections between $h_k^0(\xi)$ is limited to at most one for the reason mentioned above if $((v_b/v_a)\rho) > 1)$ and $\xi^{\Sigma\Sigma} \in [y_C^0(v_b), 1]$ at intersection points $\xi^\Sigma$, $$\left.\frac{\partial h_b^0(\xi)}{\partial \xi}\right|_{\xi=\xi^{\Sigma\Sigma}} < \left.\frac{\partial h_a^0(\xi)}{\partial \xi}\right|_{\xi=\xi^{\Sigma\Sigma}} \quad (19)$$

and $h_k^0(\xi)$ can cross another time in the interval $[y_C^0(v_b), 1]$, but they can do so only once because an additional intersection would implies $$f(\xi^\Sigma > \xi^{\Sigma\Sigma}) > (v_b/v_a)\rho \quad (20)$$

at an intersection $\xi^\Sigma$ which is impossible due to the monotonicity of $f(\xi^\Sigma)$ Finally, if $((v_b/v_a)\rho) = 1$, $\xi^{\Sigma\Sigma} \to \infty$. because $\xi^{\Sigma\Sigma}$ is outside the interval $[y_C^0(v_b), 1]$, $h_k^0(\xi)$can intersect only once. Furthermore, for this special case $h_k^0(\xi=\xi^\Sigma)$ share their tangent at their intersection.

Therefore, $\Theta_0(s_C^0)$ has at most two zeros. In addition, if $((v_b/v_a)\rho) > 1$ there are exactly two zeros and, $$h_b^0(\xi=1) < h_a^0(\xi=1) \quad (21)$$

The same logic applies to $\Theta_1(s_C^1)$.

The zeros of each $\Theta_i(s_C^{(i)})$ are evaluated numerically. First $y_C^i$ are estimated the same way we estimated $s_H^{(i)}$ with the H-step protocol. Specifically, the parameters $\tau_T^{(i)}$ are estimated with theorem 3.1 of Wang and Beaumont [20].

Subsequently $s^{(0)}(u_C)/s_T^{(0)}$ and $s^{(1)}(u_C)/s_R^{(1)}$ are estimated with theorems 3.1 and 3.8 of Wang and Beaumont [20] respectively.

The zeros of each $\Theta_i(s_C^{(i)})$ are then found. If $((v_b/v_a)\rho) \leq 1$, then there is only one zero in the interval $[y_C^0(v_b), 1]$ for $\Theta_0(s_C^0)$ and $[0, y_C^1(v_b)]$ for $\Theta_1(s_C^1)$. They can be found by dichotomy. In the special case where $((v_b/v_a)\rho) = 1$, the zero is at coordinate $\xi = \xi^{\Sigma\Sigma}$ (see proof of Lemma 1).

If $((v_b/v_a)\rho) > 1$, the number of zeros depends on $h_k^i(s_C^0)$ at one end of the search interval. Specifically if $h_b^0(s_C^0=1) > h_a^0(s_C^0=1)$, $\Theta_0(s_C^0)$ has one zero, otherwise it has two. Similarly if $h_b^1(s_C^1=0) > h_a^1(s_C^1=0)$ $\Theta_1(s_C^1)$ has one zero, otherwise it has two. Note that $h_k^i(s_C^0)$ cannot be equal at the bounds of the search interval as long as $y_C^i(v_a) \neq y_C^i(v_b)$. When there are two zeros, the coordinate $\xi^{\Sigma\Sigma}$ split the search interval in two, i.e., each zero should be in the interval delimited by $\xi^{\Sigma\Sigma}$ and the bounds of the search interval. See proof of Lemma 1 for the evaluation of $\xi^{\Sigma\Sigma}$. Once $\xi^{\Sigma\Sigma}$ has been evaluated, we find each zero by dichotomy with a precision of $10^{-6}$. The application of this procedure to the synthetic data set is illustrated in FIG. 10 (Triangles)

Figure 12A:
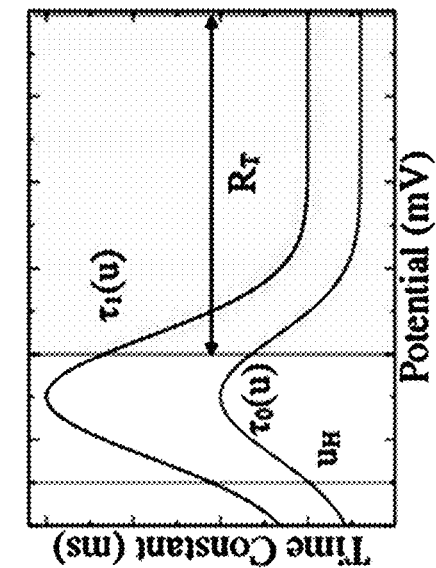
FIG. 12A shows an exemplary graph of potential vs. time illustrating the voltage clamp stimulation protocol (T-Step) suitable for time constants estimation at large potential.
Figure 12B:
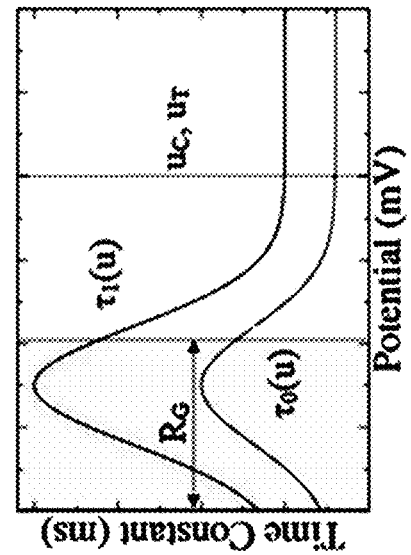
FIG. 12B shows an exemplary graph of time constant vs. potential illustrating the voltage range over which time constant can be estimated with the T-step protocol.
Figure 12C:
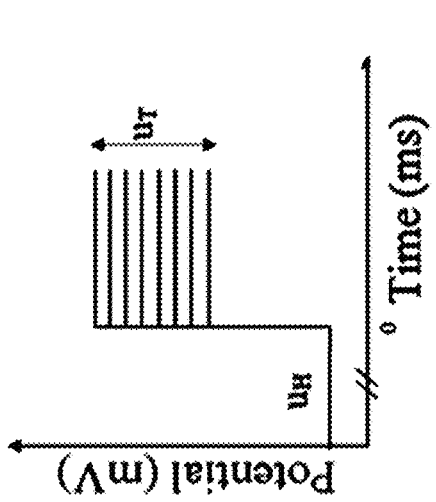
FIG. 12C shows an exemplary graph of potential vs. time illustrating a new G-step voltage clamp stimulation protocol suitable for time constants estimation, near rest potential.
Figure 12D:
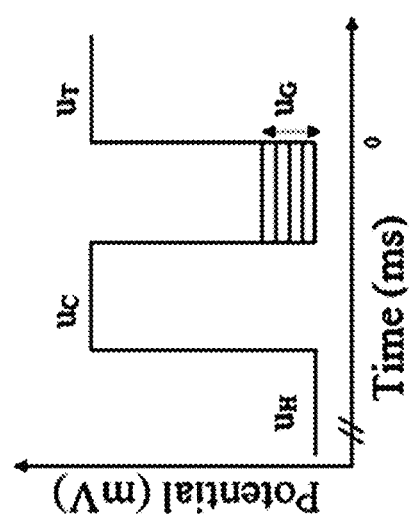
FIG. 12D shows an exemplary graph of time constant vs. potential illustrating the voltage range over which time constant can be estimated using the protocol (G-step) of FIG. 12C.
Figure 12E:
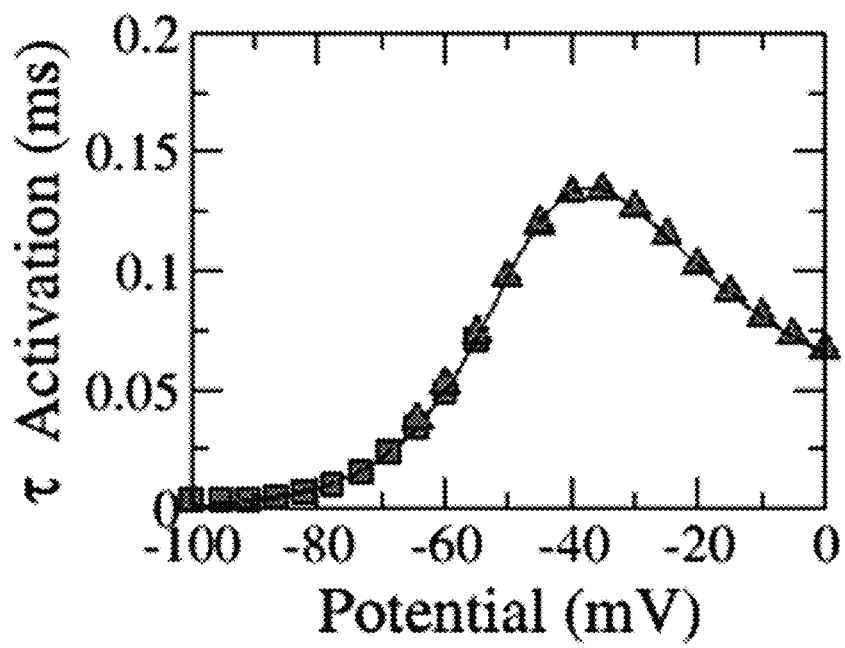
FIG. 12E shows a graph of activation time constant vs. potential estimated with data generated with the protocols of FIG. 12A.
Figure 12F:
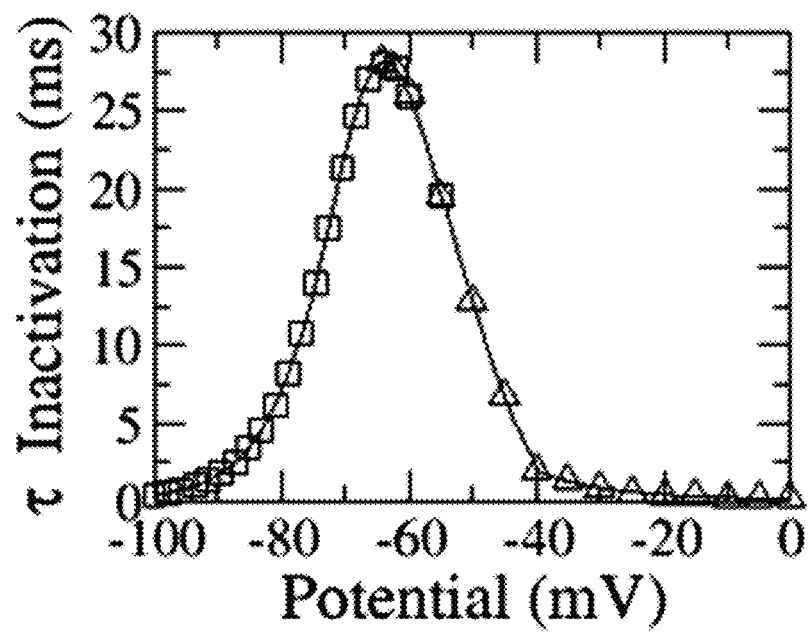
FIG. 12F shows a graph of activation time vs. potential for the new protocol of FIG. 12A (triangles), 12C (squares)

Estimation of $\tau_i(u)$ $i \in [0,1]$ The limitation raised in Part 2 can be overcome by adding voltage clamp data to the conventional data set and introducing new processing. As with steady state estimation synthetic voltage clamp data were generated with the Ebihara and Johnson model [7] which are then processed to estimate $\tau_i(u)$. The time constant for large depolarized potential are estimated similarly to the Biological data, i.e., we use theorems 4.1 and algorithm 4.4 of Wang and Beaumont [20] to estimate $\tau_i(u)$ (FIG. 12). FIG. 12A shows an exemplary graph of potential vs. time illustrating a voltage clamp stimulation protocol suitable for time constants estimation. FIG. 12B shows an exemplary graph of time constant vs. potential illustrating the voltage range where the parameters are estimated using protocol of FIG. 12A. FIG. 12C shows an exemplary graph of potential vs. time illustrating a new voltage clamp stimulation protocol suitable for time constants estimation. FIG. 12D shows an exemplary graph of time constant vs. potential illustrating the voltage range where the parameters are estimated using protocol of FIG. 12C. FIG. 12E shows a graph of activation time vs. potential for the protocols of FIG. 12A (triangles) and FIG. 12C (squares). FIG. 12F shows a graph of inactivation time vs. potential for the protocols of FIG. 12A (triangles) and FIG. 12C (squares). FIG. 12C shows a new stimulation protocol termed the G-step protocol. The protocol includes two pulses separated by a gap. Currents recorded during the test pulse are interpreted. The gap potential is varied to probe the time constant in the desired voltage range, and its duration is adjusted to obtain currents of significant magnitude during the application of the test pulse and independent from one another. The range of the protocol is denoted by $R_G$. Because with this protocol, the potential is never held for long intervals of time at large depolarized potentials and the experimentalist has the freedom to set the test pulse at any value that generate currents of significant magnitude, as long as $$\{u_T : s_1(u_T) < \varepsilon\},$$

where $\varepsilon$ is a pre-determined threshold, the limitations raised in § 2 are overcame.

In such conditions, theorems 3.1 and 3.8 of Wang and Beaumont [20] are used to evaluate the gating variables at the end of the gap. Because the steady states are known, the time constants can be obtained from (3). The squares in FIG. 12E and FIG. 12F were obtained applying this procedure.

4.3 The effect of noise on the data

Among other advantages, an important one of our inversion procedure is to better handle the ill posed nature of the problem. The method extracts the steady states, a range for $R=1/\bar{g}$ and functions of voltage representing the time constants that reproduce the data within a given tolerance. There is at least one function of voltage for each gate and for each R picked within the bounds. These functions are extracted following the inversion procedure outlined in Part 2, "Estimation of $\tau_i(u)$" provides $\tau_i(u)$. There is at least one function for each gate because for a given voltage the inversion may generate more than one value, so in general the functions may bifurcate, i.e., like a tree.

The effect of noise on the data is illustrated with a synthetic noisy data set. Voltage clamp data are generated with the Ebihara and Johnson model [7] to which we add 5% white noise. The data set is generated with stimulation protocols of FIG. 10A, FIG. 10C, FIG. 12A, and FIG. 12C, which fully constrain the gating model. The data is filtered as indicated in Part 3.

Steady states are estimated with the procedures of Part 4.2 and using data generated with the H-step and C-step protocols. The first step includes estimating $\tau_T^{(i)}$ i∈[0,1], which was done so far with theorem 3.7 of Wang and Beaumont [20]. However, estimation of $\tau_T^i$ with this theorem includes finding the minimum of an objective function that may be quite flat in the vicinity of the minimum when the problem is ill posed. We address this problem by supplementing processing with theorem 3.7 of Wang and Beaumont [20] by finding the minimum of the objective function, $$\Theta = \sum_n \sum_k \left[ I_N^{1/\lambda_0}(t_k, u_n; t_r, \tau_T^0, \tau_T^1) - E^{1/\lambda_0}(t_k, u_n; t_r) \right]^2 \quad (22)$$

$$I_N^{1/\lambda_0}(t_k, u_n; t_r, \tau_T^0, \tau_T^1) = e^{\frac{-\lambda_1(t_k - t_r)}{\lambda_0 \tau_T^1}} \left[ \frac{J(t_r, u_n) + \lambda_0/\tau_T^0 + \lambda_1/\tau_T^1}{J(t_k, u_n) + \lambda_0/\tau_T^0 + \lambda_1/\tau_T^1} \right]. \quad (23)$$

with respect to $\tau^{(i)}$, i∈[0,1], where $I_N$ is the current normalized with respect to a value taken at a reference time $t_r$, and E its experimental counterpart. The discrete variables $t_k$ and $u_n$ are the time samples, and potentials in the range of each stimulation protocol. The minimum can be found with a steepest descent with gradient, $$\nabla_\tau = [\partial/\partial(1/\tau_T^0), \partial/\partial(1/\tau_T^1)] \quad (24)$$

Figure 13A:
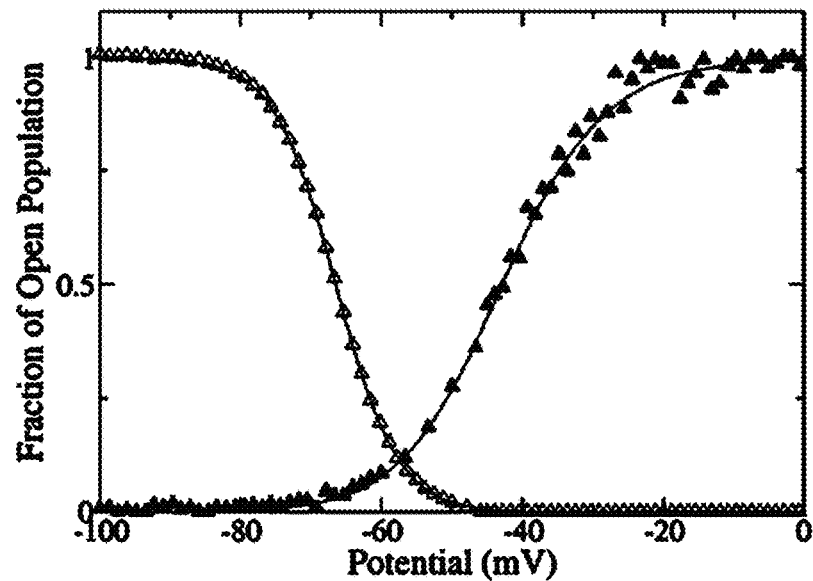
FIG. 13A is a graph of the voltage dependence of the steady state of the gating variables estimated from noisy data.

The initial value is set with theorem 3.7 of Wang and Beaumont [20]. Once $\tau_T^{(i)}$, i∈[0,1] estimated, procedures of Part 4.2 are applied on the smoothed data. The result of the steady state estimation on the noisy current is illustrated in FIG. 13A. FIG. 13A is a graph of fraction of open population vs. potential illustrating model steady states (solid lines) and estimated values (symbols) on noisy data.

Figure 13B:
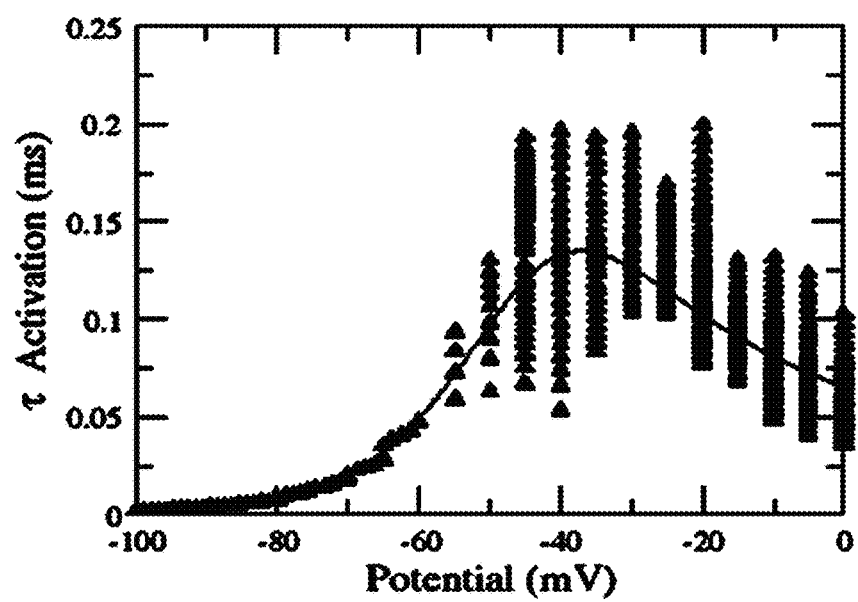
FIG. 13B shows an exemplary graph of the voltage dependence of the activation time constant time estimated from noisy data.
Figure 13C:
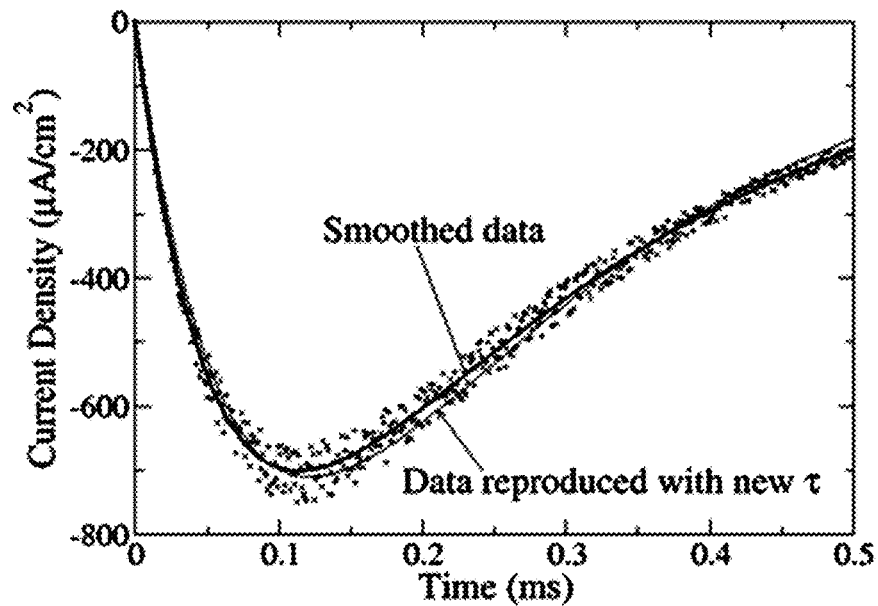
FIG. 13C shows an exemplary graph of current density vs. time illustrating typical noisy current with its filtered version, and a current produced by a model the parameters of which were obtained through the inversion.
Figure 13D:
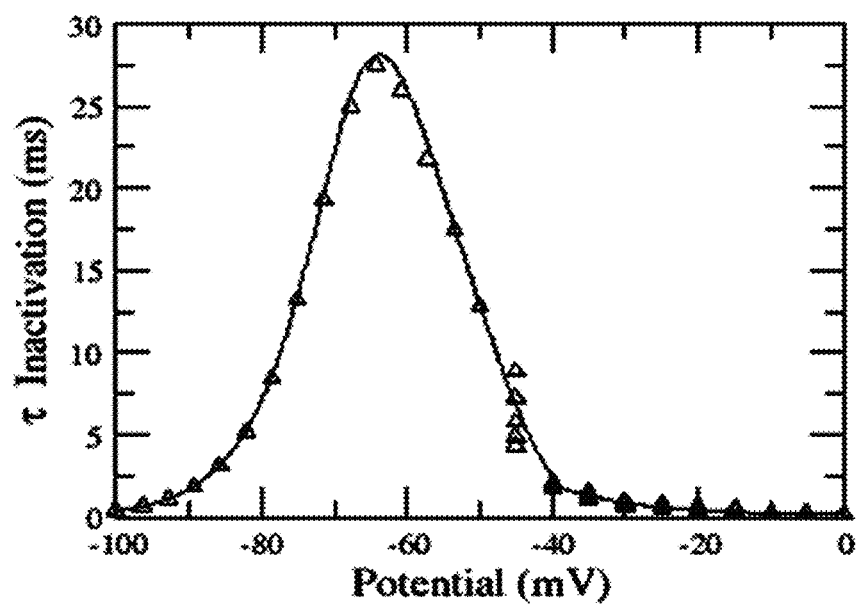
FIG. 13D shows an exemplary graph of inactivation time vs. potential illustrating time constants as well as estimated from noisy data.
Figure 14:
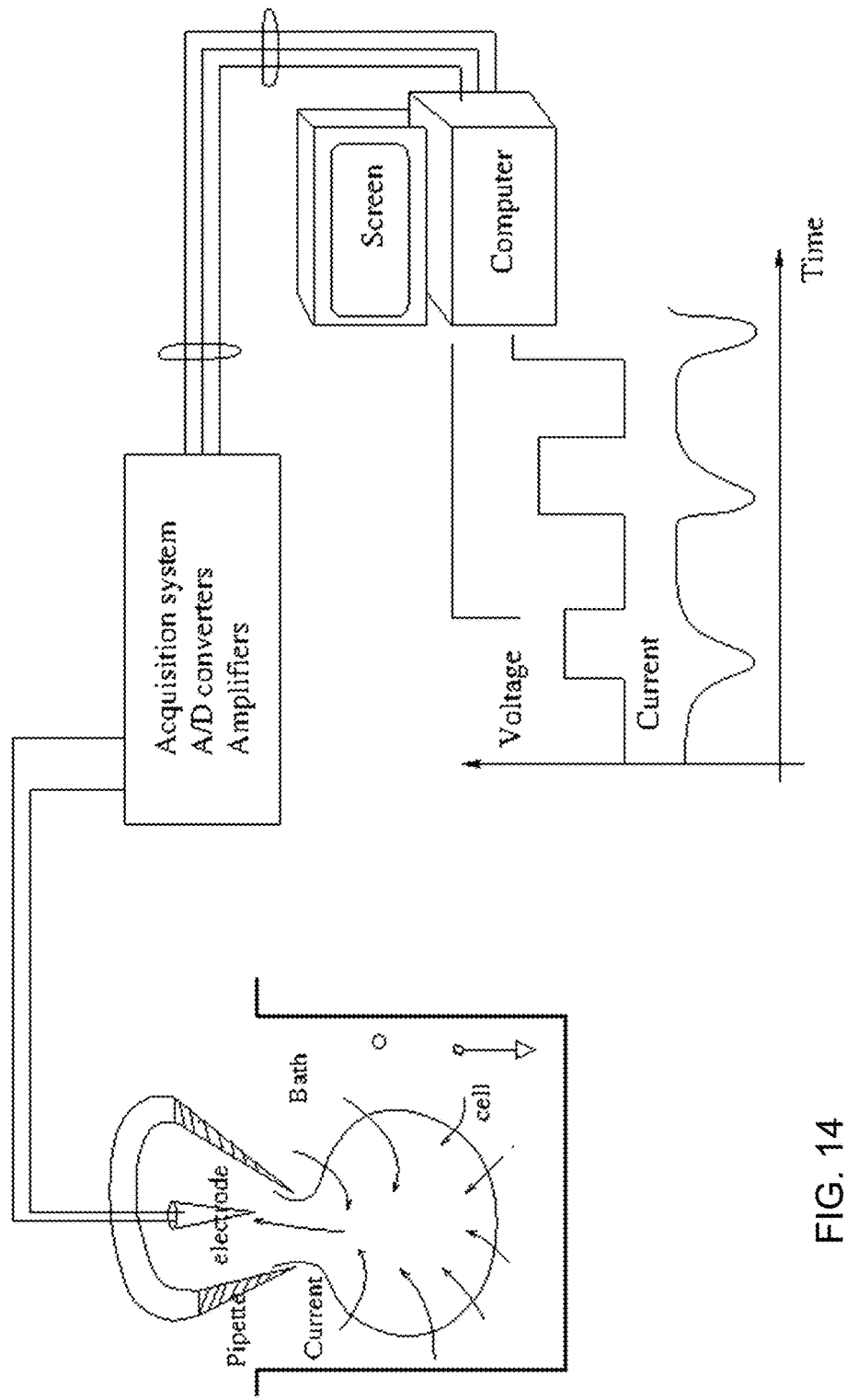
FIG. 14 shows a block diagram of a system suitable to perform the new method.

Time constants are estimated with theorem 4.1 and algorithm 4.4 of Wang and Beaumont [20] applied to the data envelope generated by adding ±5% to the data. This converts the lines of the jaw in the inversion of $y_i(u)$ i∈[0,1] to ribbons, which widens the invertible range. In this case, the inversion is now more complicated. Note that, due to the nonlinearity of the model, the bounds on the time constants at each potential are not necessarily on the frontier of the bands of invertible values. Thus, once the bound on R is defined, we sweep R within its bounds with 100 samples, and estimate $\tau_T^{(i)}$, i∈[0,1] for each sample. The values obtained are displayed with a symbol in FIG. 13B and FIG. 13D. FIG. 13B shows an exemplary graph of activation time vs. potential illustrating time constants (solid lines) as well as estimated values on noisy data (symbols). FIG. 13D shows an exemplary graph of inactivation time vs. potential illustrating time constants (solid lines) as well as estimated values on noisy data (symbols). FIG. 13B shows the inversion predicts a wide range of acceptable activation time constants. FIG. 13C shows an exemplary graph of current density vs. time illustrating typical noisy current with its filtered version (thick black line), and a current produced by a model (thin black line) the parameters of which were obtained through the inversion. FIG. 13C further supports this point. It shows the smoothed data within the noise (5%), and a current generated with a model having a conductance of $\bar{g}$=31 mS/cm$^2$ and time constants at test potential of $\tau_0$=0.0509 ms and $\tau_1$=0.3028 ms, quite different from the original model, with $\bar{g}$=23 mS/cm$^2$ and time constants at test potential of $\tau_0$=0.08 ms and $\tau_1$=0.25 ms. The parameters of the voltage clamp stimulation are $u_H$=−100 mV and $u_T$=−10 mV. The model $\bar{g}$=23 mS, and for this $u_T$ $\tau_0(-10)$=0.08 ms and $\tau_1(-10)$=0.25, which values are within the range of the inversion. Clearly as judged by the gaph of FIG. 13B, a wide rang of parameters can be used to reproduce this current.

Note the symbols of FIG. 13B and FIG. 13D represent a space where functions of voltage can be found which represent time constants that reproduce the data. To extract these functions a value of R should be picked within the bounds, and followed by application of the inversion procedure. This procedure handles the effect of noise in a novel way. As the noise on the data increases, the bounds on R widen, and increase the variety of time constants that can reproduce the data. Furthermore, because inversion is performed for each voltage of the stimulation protocol, the effect of noise is taken into consideration locally. The functions extracted are not just a simple offset of basic functions, as for each R, they may vary significantly.

Part 5 Discussion

There are three elements of concern when dealing with the estimation of the parameters of nonlinear ODEs whether or not: (i) the data constrain the model, (ii) has an optimal solution been reached, and (iii) if the problem ill posed or well posed.

1. Constrained. As illustrated in the treatment of Biological data an important advantage of our approach is its ability to determine, a priori, whether the data constrains the Hodgkin-Huxley gating model. This advantage stems from the fact that the data for some model components (steady states and time constants) is inverted, and bound some of the other components (conductance). This has two direct implications for the modeling method in the field. First, if the data does not sufficiently constrain the gating model, several models capable of reproducing it can be extracted. These could then be studied with a bifurcation analysis. Second, the method enables us to readily investigate stimulation protocols that can generate complete data sets with respect to the inversion of the Hodgkin-Huxley formalism. Introducing the 4 complementary stimulation protocols illustrated in FIG. 10A, FIG. 10C, FIG. 12A and FIG. 12C. FIG. 10A, FIG. 10C, FIG. 12A and FIG. 12C merely show exemplary suitable protocols for use with the new method and system described herein. Any suitable protocol that can generate a complete data set for inversion of the Hodgkin-Huxley formalism can be used. However, an advantage of the protocols presented hereinabove is their practicality because they take into consideration experimental constraints.

Interestingly, it was established that currents generated exclusively with the H-step and T-step protocols cannot constitute a complete data set with respect to the inversion of the Hodgkin Huxley formalism. This does not mean currents produced by these protocols are not useful. One can, for example, draw conclusions on an intervention, e.g., the effect of a drug comparing currents collected with these protocols with and without drug binding to the channel. The problem stressed herein includes the estimation of the parameters (including functions of voltage) of the Hodgkin-Huxley formalism from experimental data, which shares concerns with the estimation of any parameters for any differential equation from experimental data.

2. Optimal. Typically, parameter estimation for nonlinear ODE models is achieved with nonlinear least square fitting. For example, Willms et al. [21] and Lee et al. [12] have presented implementations of such an approach for the Hodgkin-Huxley formalism. An inherent difficulty of such an approach is that, because most of the time the shape of the objective function subjected to minimization is not known, one can never guarantee an optimal inverse solution is reached. Here, this difficulty is avoided by determining, for each objective function to minimize, the number if their extrema, and presented strategies to locate them. Indeed, the new method and system described herein alleviates several limitations inherent to nonlinear least square fitting.

3. Ill-posed. Our approach allows to cope with the ill-posed nature of the estimation problem in a novel way. This is illustrated in section 4.3 where, from only 5% noise on the data it could be determined that this can generate 50% change on the activation time constant, even if the data set is complete. To find the range on the inverse solution, we first bounded the parameter R, then the inverse solutions within these bounds was explored. Due to the nonlinearity of the Hodgkin-Huxley gating model, the time constants at each data point deviating the most from the model are not necessarily associated to the values of R on the frontier of the invertible range. Indeed, our extensive exploration of the inverse solution enabled us to find a wider range for the inverse solution than initially suspected.

One may argue that a similar effect could be achieved formulating a model through nonlinear fitting and then perturbing the functions. However to achieve this with the resolution in voltage that is related to the number of samples taken during acquisition, one would need to use functions including a large number of parameters. In such case the minimization becomes problematic because the algorithm may be trapped in local minima. Indeed as the number of parameters increase it becomes unlikely to find the optimal solutions.

Another group [12] reached a different conclusion. With 5% to 15% noise on the data they reported only 12% variation on the activation time constant. Their approach is based on the minimization of 3 nonlinear objective functions, and their statistics follow from 100,000 repetitions of the minimization with random start-up values. The discrepancy between the results is probably because their objective functions may have several local minima providing good inverse solutions that have not been explored during minimization. Although the number of trials is large, the dimension of their search space is also very large, i.e., a parameter, plus 3 others for each potential. Thus, without information on the shape of the objective function, it is difficult to know whether the start-up values for minimization allow for a full exploration of the search space.

Finally, this approach may have a number of implications for multiscale modeling of bioelectric phenomena. For example, changes on steady state activation, and activation time constant of the order of magnitude shown in FIG. 13A, FIG. 13B, FIG. 13C, and FIG. 13D can produce a wide range of predictions regarding vortex dynamici [2] in a monolayer of cardiac cells. While parameter sensitivity analysis as described by Sobie [19] has a number of advantages, the combination of inversion and bifurcation analysis above mentioned may enable one to uncover a range of model predictions that would not be suspected otherwise. The application of such an approach in a multiscale modeling framework where voltage clamp data gathered in cell expression systems is analyzed may, for example, allow for capitalization on the human genome in a novel way to elucidate the mechanisms of inherited arrhythmias.

Applications: Data at the origin of the estimation can be generated in different ways. The most common method includes isolating cells with an enzymatic solution and then stimulating them with electrodes attached to an electronic control system that applies a voltage and monitor current. A chemical agent blocking the channel in question is typically inserted in bathing solution. Currents are recorded in the presence and absence of the blocking agent. The analysis can be performed on the data obtained by subtracting current obtain with the blocking agent from the one without the blocking one.

Recording could be done with pipettes. In this case currents could be recorded in a cell or patch excised from cells. Also, configurations described in Hamill et al (1981) would work.

For larger cells currents could be obtained with one or two microelectrodes impaled in isolated cells (Finkel 1985a 198b)

The method is applicable to any cell as long as it can be isolated, and the protein in question could be blocked with a chemical agent. This includes stem cells, or cells differentiated in-vitro by any means.

It is contemplated that the method will be particularly useful to characterize the effect of drugs on membrane channels. Recordings of currents produced by target channels could be repeated in the presence and absence of drugs. The method could be applied on such data set to generate an Hodgkin Huxley formalism of a channel bound to a drug, and this way enabling to make predictions on the physiological effect of a drug or its toxicity.

This could be particularly powerful for cells harvested on an individual cell and differentiated in-vitro. This opens the possibility to make individualized predictions.

So far the new method and system has been applied to proteins that are voltage gated, but the method could also be applied to any other endogenous or exogenous factors modifying current kinetics through a change in protein configuration.

In addition to characterize the effect of drugs on current kinetics, the method could also be applied to determine how various stress, e.g.: changes in pH, intracellular calcium concentration, lactic acid, oxygen deprivation, or exposure to magnetic field alters the function of a protein by recording current with the methods above described hereinabove after the application of the stress.

One or more processes of the new method and system described herein are typically run on any suitable type of computer programmed to perform the one or more processes. Suitable computers include, for example, personal computers, computer workstations, any suitable portable computer (e.g. laptop, notebook, tablet, etc.), typically including one or more microprocessor or an equivalent computational element in firmware or software (e.g. programmed gate arrays).

It is understood that the protocols described herein include both voltage parameters and time parameters. For example, it is understood that a voltage difference across a cell membrane will typically be held substantially constant for a time interval which is defined by the protocol. Similarly, it understood that following a step change in the voltage difference, the new voltage difference will also typically be held substantially constant for a time also determined by the protocol.

When acquiring voltage and current data at an interval, it is understood that the absolute or relative time each measurement was acquired is known based on the time interval. Alternatively, each measurement of voltage and current can be recorded to memory along with a time stamp.

Software and/or data of the processes described hereinabove can be supplied and stored on a computer readable non-transitory storage medium. A computer readable non-transitory storage medium as non-transitory data storage includes any data stored on any suitable media in a non-fleeting manner. Such data storage includes any suitable computer readable non-transitory storage medium, including, but not limited to hard drives, non-volatile RAM, SSD devices, CDs, DVDs, etc.

It will be appreciated that variants of the above-disclosed and other features and functions, or alternatives thereof, may be combined into many other different systems or applications. Various presently unforeseen or unanticipated alternatives, modifications, variations, or improvements therein may be subsequently made by those skilled in the art which are also intended to be encompassed by the following claims.

REFERENCES

[1] Bassingthwaighte, J.: NSR physiome project. http://www.physiome.org, University of Washington (2012).

[2] Beaumont, J., Davidenko, N., Davidenko, J. M., Jalife, J.: Spiral waves in two-dimensional models of ventricular muscle: Formation of a stationary core. Biophysical Journal 75(1), 1-14 (1998).

[3] Beaumont, J., Roberge, F., Lemieux, D.: Estimation of the steady-state characteristics of the Hodgkin-Huxley model from voltage-clamp data. Mathematical Biosciences 115(2), 145-186 (1993).

[4] Beaumont, J., Roberge, F., Leon, L.: On the interpretation of voltage-clamp data using the Hodgkin-Huxley Model. Mathematical Biosciences 115(1), 65-101 (1993).

[5] Bower, J., Beeman, D.: Genesis. http//:genesis-sim.org/, University of Texas and University of Colorado (2012).

[6] Cordeiro, J. M., Mazza, M., Goodrow, R., Ulahannan, N., Antzelevitch, C., Di Diego, J. M.: Functionally distinct sodium channels in ventricular epicardial and endocardial cells contribute to a greater sensitivity of the epicardium to electrical depression. American Journal of Physiology Heart and Circulatory Physiology 295(1), H154-H162 (2008).

[7] Ebihara, L., Johnson, E.: Fast sodium current in cardiac muscle. a quantitative description. Biophysical Journal 32(2), 779-790 (1980).

[8] Ermentrout, G. B., Terman, D. H., Ermentrout, G. B., Terman, D. H.: The Hodgkin-Huxley Equations, *Interdisciplinary Applied Mathematics*, vol. 35. Springer New York (2010).

[9] Grandi, E., Pasqualini, F., Bers, D.: A novel computational model of the human ventricular action potential and ca transient. J. Molecular and Cellular Cardiology 48, 112-121 (2010).

[10] Hines, M., Moore, J., Carnevale, T., Morse, T., Shepherd, G.: Neuron. http://www.neuron.yale.edu/neuron, Yale University (2012).

[11] Hodgkin, A. L., Huxley, A. F.: A quantitative description of membrane current and its application to conduction an excitable nerve. The Journal of Physiology 117, 500-544 (1952).

[12] Lee, J., Smaill, B., Smith, N.: Hodgkin-Huxley type ion channel characterization: An improved method of voltage clamp experiment parameter estimation. Journal of Theoretical Biology 242(1), 123-134 (2006).

[13] Loew, L.: Vcell: The virtual cell. http://www.nrcam.uchc.edu/about/about_vcell.html, University of Connecticut (2012).

[14] McCormick, D., Shu, Y., Yu, Y.: Neurophysiology: Hodgkin and huxley model—still standing? Nature 445, E1E2 (2007).

[15] Murphy, L., Renodin, D., Antzelevitch, C., Di Diego, J. M., Cordeiro, J. M.: Extracellular proton depression of peak and late na+ current in the canine left ventricle. American Journal of Physiology Heart and Circulatory Physiology 301(3), H936-H944 (2011).

[16] Nielsen, P.: Cellml. International collaborative effort, University of Auckland (2012).

[17] Noble, D., Garny, A., Noble, P. J.: How the Hodgkin-Huxley equations inspired the cardiac physiome project. The Journal of Physiology pp. 1-30 (2012).

[18] O'hara, T., Virag, L., A., V., Y., R.: Simulation of the undiseased human cardiac ventricular action potential: Model formulation and experimental validation. PLoS Computational Biology 7(5), e1002,061-e1002,090 (2011).

[19] Sobie, E.: Parameter sensitivity analysis in electrophysiological models using multivariable regression. Biophysical Journal 96(4), 1264-1274 (2009).

[20] Wang, G., Beaumont, J.: Parameter Estimation of the Hodgkin-Huxley Gating Model: An Inversion Procedure. SIAM Journal on Applied Mathematics 64(4), 1249-1267 (2004).

[21] Willms, A., Baro, D., Harris-Warrick, R., Guckenheimer, J.: An Improved Parameter Estimation Method for Hodgkin-Huxley Models. Journal of Computational Neuroscience 6, 145-168 (1999).

[22] O. P. Hamill, A. Marty, E. Neher, B. Sackmann, and F. J. Sigworth, Improved patch-clamp techniques for high-resolution current recording from cells and cell-free membrane patches Pflugers Arch., 1981; 391(2), pp. 85-100.

[23] Finkel, A. S. and Redman S. J. Optimal Voltage Clamping With Single Microelectrode in: Voltage and Patch Clamping with Microelectrodes 1985, pp 95-120.

[24] Finkel A. S. and Cage W. Conventional Voltage Clamping With Two Intracellular Microelectrodes in: Voltage and Patch Clamping with Microelectrodes 1985, p. 47-94.

I claim:

1. A method to quantify a steady state functions of voltage of a gating variable of a Hodgkin Huxley formalism of a cell comprising the steps of:

provide an electrophysiology apparatus configured to provide a voltage difference across a cell membrane of a cell and to measure a current through said cell membrane and a computer configured to run one or more processes including an inversion process of a set of underlying ordinary differential equations of a Hodgkin-Huxley model wherein said inversion process is defined by the equation:

$$\left[\frac{y_C^{(i)}(v_a) - s_C^{(i)}}{s_H^{(i)} - s_C^{(i)}}\right]^{\frac{1}{v_a}} = \left[\frac{y_C^{(i)}(v_b) - s_C^{(i)}}{s_H^{(i)} - s_C^{(i)}}\right]^{\frac{1}{v_b}}, i \in [0,1]$$

where $v_a$, $v_b$: are time interval of application of the conditioning voltage of a C-step voltage clamp stimulation, i: indexes the gating variables of an Hodgkin-Huxley formalism, $y_c^{(i)}(v)$: $i^{th}$ gating variable, $i \in [0,1]$, evaluated at the end of the conditioning pulse of voltage $u_C$ and time interval of its application either $v_a$ or $v_b$, $s_C^{(i)}, s_H^{(i)}$ steady state function of voltage of each gating variable evaluated at the conditioning ($u_C$), and holding $s(u_H)$ voltages respectively, of a C-Step voltage clamp stimulation protocol;
applying said voltage difference across said cell membrane according to each protocol, and in any order:
a H-step voltage clamp stimulation protocol, and
a C-step voltage clamp stimulation protocol comprising:
applying a fixed holding voltage $u_H$, followed by applying successive conditioning pulses at a plurality of stepped conditioning voltages $u_C$ and time intervals of application, $v_a$ and $v_b$, of the conditioning voltage, following each step of said steps of conditioning pulses, applying a test voltage $u_T$ during which test voltage a test current is measured, and wherein said plurality of stepped conditioning voltage $u_C$ are higher voltage than said fixed holding voltage $u_H$,
identifying a voltage range $R_C$ of said stepped conditioning voltage $u_C$ where the channel exhibits measurable and independent currents during the test pulse, with changes of conditioning voltage $u_c$ and time intervals $v_a$, $v_b$;
For a first time interval of application of said conditioning voltage $v_a$, estimating a first $y_C^{(i)}(v_a)$ based on said inversion process, and changing said conditioning voltage and repeating said step of applying until the voltage range $R_C$ is found, where measured currents during the test pulse are measurable and independent from one another when the conditioning voltage and its time interval of application are changed;
for a second time interval of application of $u_C$, $v_b$, repeating said step of estimating to estimate a second different $y_C^{(i)}(v_b)$;
calculating a voltage dependence of the steady state functions $s_C^{(i)}$ by solving for the zeros of said objective function, using first $y_C^{(i)}(v_a)$ and second $y_C^{(i)}(v_b)$;
generating a data set as a solution of said set of underlying ordinary differential equations, said data set comprising a set of said voltage difference, and a measured current from said H-step voltage clamp stimulation protocol and said C-step voltage clamp stimulation protocol; and
estimating by said inversion process a set of gating parameters comprising a steady state as a function of voltage based on said data set to quantify said steady state function of voltage of a gating variable an Hodgkin Huxley formalism channel availability of said cell.

2. The method of claim 1, wherein said test voltage is higher than both of said holding voltage and said conditioning voltage.

3. The method of claim 1, wherein said step of estimating by said inversion process comprises evaluating $y_C^{(i)}(v_k)$ from a plurality of test currents recorded during the application of the test pulse, followed by solving for $s_C^{(i)}$ at each conditioning voltage.

4. The method of claim 1, wherein there are at most two zeros of the objective function.

5. The method of claim 4, wherein only one of said at most 2 solutions is consistent with a Hodgkin-Huxley formalism.

6. The method of claim 1, wherein said objective function is defined by the equation:

$$\Theta_i(s_C^i) = h_a^i(s_C^i) - h_b^i(s_C^i), h_k^i(s_C^i) = \left[\frac{s_C^i - y_C^i(v_k)}{s_C^i - s_H^i}\right]^{\frac{1}{v_k}},$$

where $\Theta_i(S_C^i)$, $i \in [0,1]$, are the objective functions, $h_k^i(S_k^i)$, $k \in [a,b]$, intermediary functions.

7. The method of claim 1, wherein said step of estimating of said C-step voltage clamp stimulation protocol comprises estimating as if a measured test current were acquired by an H-step protocol.

8. The method of claim 7, wherein said step of estimating of said of estimating as if a measured test current were acquired by an H-step protocol comprises the equations:

$$I_N^{\frac{1}{\lambda_i}}(t, u; t_r, u_T) - 1 = \theta_a\left(-\lambda_i \frac{dI_N(t, u; t_r, u_T)}{dt} + J(t = t_r, u; u_T)\right) - \theta_b \int_{t_r}^{t} I_N(t, u; t_r, u_T) dt,$$

where $\lambda_i$ is a number of gating particles of a $i^{th}$ gating variable, and $\theta_a$, $\theta_b$ parameters depending on constants of the Hodgkin-Husley model, I(t) is a membrane current, $u_T$ is a test voltage, $I_N$ is a current normalized with respect to a sample taken at a time $t=t_r$, and I (t) is a membrane current derivative normalized with respect to a current I(t)'

$$\frac{s_i(u)}{s_T^{(i)}} = 1 - \frac{J(t, u; u_T) + \lambda_\tau / \tau_T^{(t)}(1 + \varepsilon_{\bar{\imath}}(t))}{J(t, u; u_T) + \lambda_i / \tau_T^{(i)} + \lambda_\tau / \tau_T^{(t)}(1 - \varepsilon_{\bar{\imath}}(t))} e^{t/\tau_T^{(i)}}$$

where $\bar{\imath}$ is the i complement, $\varepsilon_{\bar{\imath}}(t)$ is an error function associated to the $\bar{\imath}^{th}$ gating variable, $s_i(u)$ the steady state function of voltage of a $i^{th}$ gating variable, the same function evaluated at test voltage $u_T$, and $\tau_T^{(i)}$ is a time constant of a $i^{th}$ gating variable evaluated at test voltage $u_T$, and $$\frac{s_\tau(u)}{s_R^{(\tau)}} = \left[\frac{I(t, u, u_T)}{I(t, u = u_R; u_T)}\right]^{-\frac{1}{\lambda_\tau}} \left[\frac{J(t, u; u_T) + \frac{\lambda_i}{\tau_T^{(i)}} + \frac{\lambda_\tau}{\tau_T^{(\tau)}}}{J(t; u_R, u_T) + \frac{\lambda_i}{\tau_T^{(i)}} + \frac{\lambda_\tau}{\tau_T^{(\tau)}}}\right]^{\frac{\lambda_i}{\lambda_\tau}}$$

where $s_{\bar{\imath}}(u)$ $\bar{\imath} \in [0,1]$ is the steady state function of voltage of the $\bar{\imath}^{th}$ gating variable, and $s_R^{(i)}$ the same function evaluated at a reference voltage $u_R$.

* * * * *